US011679053B2

(12) United States Patent
Nordgren et al.

(10) Patent No.: US 11,679,053 B2
(45) Date of Patent: Jun. 20, 2023

(54) BODY PART FIXATION DEVICE WITH PITCH AND/OR ROLL ADJUSTMENT

(71) Applicant: Medtec LLC, Orange City, IA (US)

(72) Inventors: Gregory Nephi Nordgren, North Liberty, IA (US); William Louis Barnat, Mount Holly, NJ (US)

(73) Assignee: MEDTEC LLC, Orange City, IA (US)

( * ) Notice: Subject to any disclaimer, the term of this patent is extended or adjusted under 35 U.S.C. 154(b) by 904 days.

(21) Appl. No.: 15/859,993

(22) Filed: Jan. 2, 2018

(65) Prior Publication Data
US 2018/0235824 A1 Aug. 23, 2018

Related U.S. Application Data

(60) Provisional application No. 62/460,389, filed on Feb. 17, 2017.

(51) Int. Cl.
*A61G 13/12* (2006.01)
*A61B 90/14* (2016.01)
(Continued)

(52) U.S. Cl.
CPC ............ *A61G 13/121* (2013.01); *A61B 90/14* (2016.02); *A61F 5/3707* (2013.01); *A61B 90/18* (2016.02); *A61B 2090/101* (2016.02)

(58) Field of Classification Search
CPC ....... A61B 90/18; A61B 5/055; A61B 6/0428; A61B 6/0407; A61B 90/14; A61B 2090/101; A61B 6/04; A61B 6/0421; A61B 90/10; A61G 13/12; A61G 13/1295; A61G 13/121; A61G 13/1215; A61G 13/128; A61G 13/1285; A61G 7/07; A61G 7/072; A61G 7/075; A61G 7/0755; A61G 7/1061;
(Continued)

(56) References Cited

U.S. PATENT DOCUMENTS 3,957,262 A 5/1976 McReynolds
4,455,698 A * 6/1984 Eary, Sr. ............... A47C 20/023
5/632
(Continued)

FOREIGN PATENT DOCUMENTS

CA 2633680 A1 7/2007
CN 1799499 A * 7/2006 ........... A61B 5/0555
(Continued)

OTHER PUBLICATIONS

High-Accuracy Localization Using Implanted Fiducials—by Northwest Medical Physics Equipment, Lynnwood, WA. Tech Times, vol. 8, Issue 2, Fall 2002, 2 pages.
(Continued)

*Primary Examiner* — Ophelia A Hawthorne
*Assistant Examiner* — Michael Milo
(74) *Attorney, Agent, or Firm* — Snyder, Clark, Lesch & Chung, LLP

(57) ABSTRACT

A structure for positioning a body part includes a support base, and a shell frame having an inner surface configured to a shape of the body part. The shell frame is further configured to ride upon the support base, or upon a carriage that further rides upon the support base, to enable a pitch and/or a roll of the shell frame to be adjusted relative to the support base.

12 Claims, 34 Drawing Sheets

(51) Int. Cl.
*A61F 5/37* (2006.01)
*A61B 90/10* (2016.01)
*A61B 90/18* (2016.01)

(58) Field of Classification Search
CPC ............... A61G 7/1082; A61G 7/1084; A61G 13/1205; A61G 13/126; A61G 7/065; A61G 7/1049; A61F 5/04; A61F 5/042; A61F 5/048; A61F 5/055; A61F 5/3707; A61F 5/05883; A61F 5/05891; A61F 5/37; A61F 5/3761; A61F 5/3769; A61H 1/0292; A61H 1/0296; A61H 1/0218; A61H 1/0222; A61H 1/0229; A61H 1/0281; A61H 2201/1604; A61H 2201/1607; A61H 2201/1609; A61H 2201/1611; A61H 2201/1614; A61H 2201/1616
USPC ....................... 128/845, 857; 5/622
See application file for complete search history.

(56) References Cited

U.S. PATENT DOCUMENTS

| | | | | |
|---|---|---|---|---|
| 4,504,050 | A * | 3/1985 | Osborne | A61G 13/12 378/179 |
| 4,757,983 | A * | 7/1988 | Ray | A61G 13/12 5/640 |
| 4,979,519 | A * | 12/1990 | Chavarria | A61B 6/501 128/857 |
| 5,370,117 | A | 12/1994 | McLaurin, Jr. | |
| 5,537,704 | A * | 7/1996 | Dinkler | A61B 90/14 5/643 |
| 5,553,112 | A | 9/1996 | Hardy et al. | |
| 5,566,681 | A | 10/1996 | Manwaring et al. | |
| 5,595,191 | A | 1/1997 | Kirk | |
| 5,702,406 | A | 12/1997 | Vilsmeier et al. | |
| 5,775,337 | A | 7/1998 | Hauger et al. | |
| 5,782,244 | A | 7/1998 | Kostich | |
| 5,800,353 | A | 9/1998 | McLaurin, Jr. | |
| 6,315,783 | B1 * | 11/2001 | Katz | A61B 90/14 606/130 |
| 6,460,207 | B1 | 10/2002 | Papay et al. | |
| 6,698,045 | B1 | 3/2004 | Coppens et al. | |
| 7,073,508 | B2 | 7/2006 | Moyers | |
| 7,103,930 | B1 | 9/2006 | Addesso-Dodd | |
| 7,290,548 | B2 | 11/2007 | Ungemach et al. | |
| 7,802,576 | B2 | 9/2010 | Cuypers et al. | |
| 8,100,132 | B2 | 1/2012 | Markstroem | |
| 8,567,405 | B2 | 10/2013 | Arn et al. | |
| 8,640,289 | B2 * | 2/2014 | Reeder, Jr. | A47D 13/08 5/640 |
| 10,130,542 | B1 * | 11/2018 | Strawder | A61G 13/121 |
| 2002/0038659 | A1 | 4/2002 | Al-Kassim | |
| 2004/0159325 | A1 | 8/2004 | Korver et al. | |
| 2009/0025146 | A1 * | 1/2009 | Mazzei | A61G 13/121 348/78 |
| 2010/0000549 | A1 | 1/2010 | Nieberding | |
| 2011/0265264 | A1 * | 11/2011 | Reeder, Jr. | A47D 15/008 5/640 |
| 2015/0047652 | A1 | 2/2015 | De Mooij | |
| 2015/0053213 | A1 | 2/2015 | Nieberding | |
| 2015/0096570 | A1 | 4/2015 | Noras | |
| 2015/0202073 | A1 | 7/2015 | Zacharopoulos et al. | |
| 2016/0095739 | A1 | 4/2016 | Coppens et al. | |
| 2016/0206395 | A1 * | 7/2016 | Coppens | A61F 5/05858 |
| 2016/0213337 | A1 * | 7/2016 | Coppens | A61B 6/04 |
| 2017/0252201 | A1 * | 9/2017 | De Gruytere | A61N 5/1077 |
| 2018/0207045 | A1 * | 7/2018 | Le | A61G 13/121 |
| 2019/0046394 | A1 * | 2/2019 | Lurie | A61G 1/04 |

FOREIGN PATENT DOCUMENTS

| | | |
|---|---|---|
| JP | 2002291731 A | 10/2002 |
| JP | 2002345906 A | 12/2002 |
| JP | 2009000321 A | 1/2009 |
| JP | 2014097094 A | 5/2014 |

OTHER PUBLICATIONS

Specialty systems to further enhance the benefits of the Type-S. Advanced Patient Positioning and Fixation. Astro 2004. Medtec. 2 pages.
Uni-frame head & neck immobilization system. Med-Tec Inc. Medtec 2003 Catalog. 3 pages.
Civco: Shell, Prone Head Support. Dwg. No. MT-202-15. 2009, 1 page.
Freedom Prone Immobilization System. CDR Systems. Retrieved online http://www.cdrsys.ca/prone-head.html. Print date Jan. 9, 2018, 2 pages.
Prone Head Holder, Uni-frame. Civco Radiotherapy. Retrieved online http://civcort.com/ro/head-neck/uniframe-baseplates/Uni-frame-Prone-Head-Holder.htm. Print date Jan. 9, 2018, 2 pages.
Civco Solutions Guide vol. 3.0. Civco Radiotherapy. 2016, 116 pages.

* cited by examiner

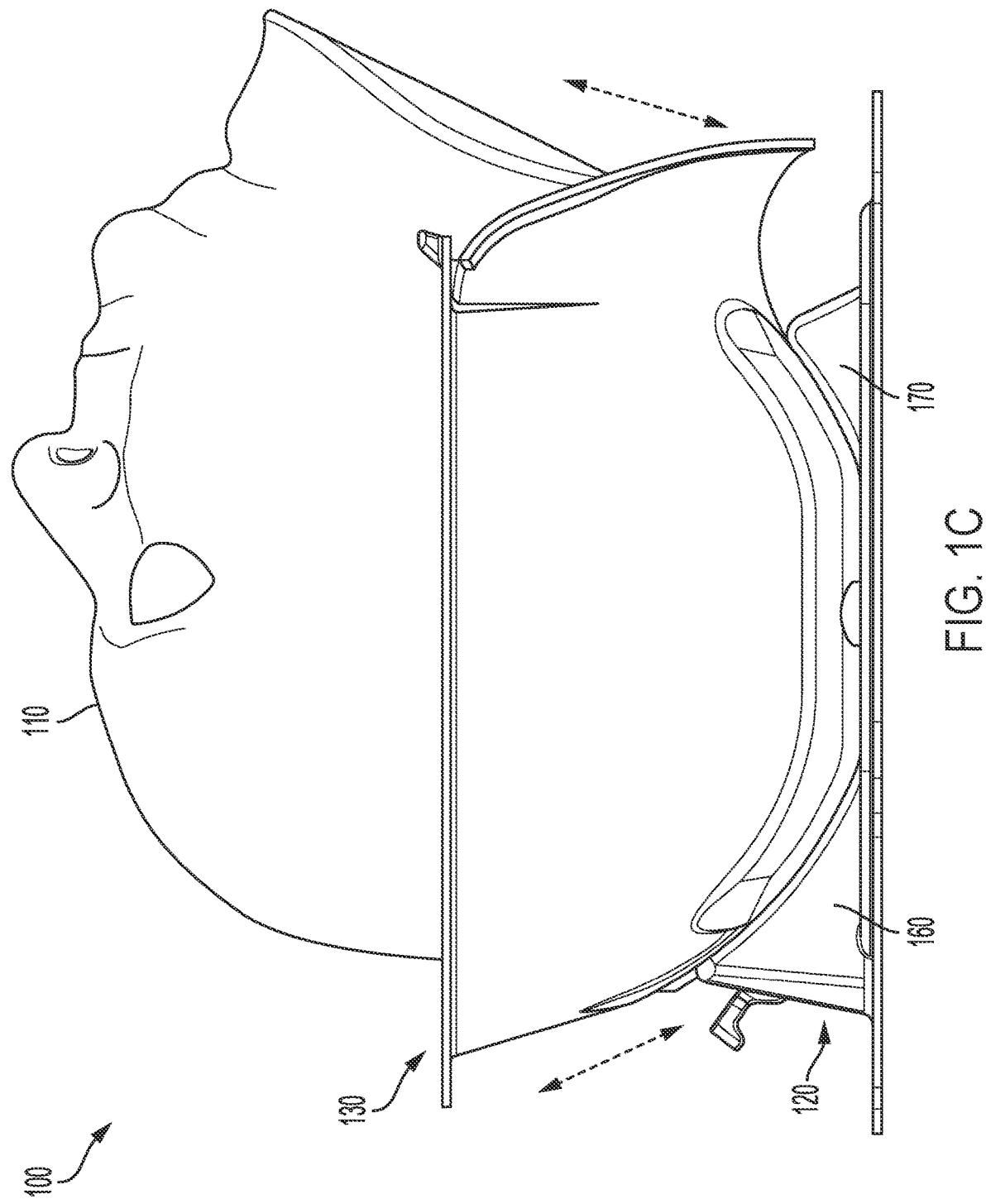

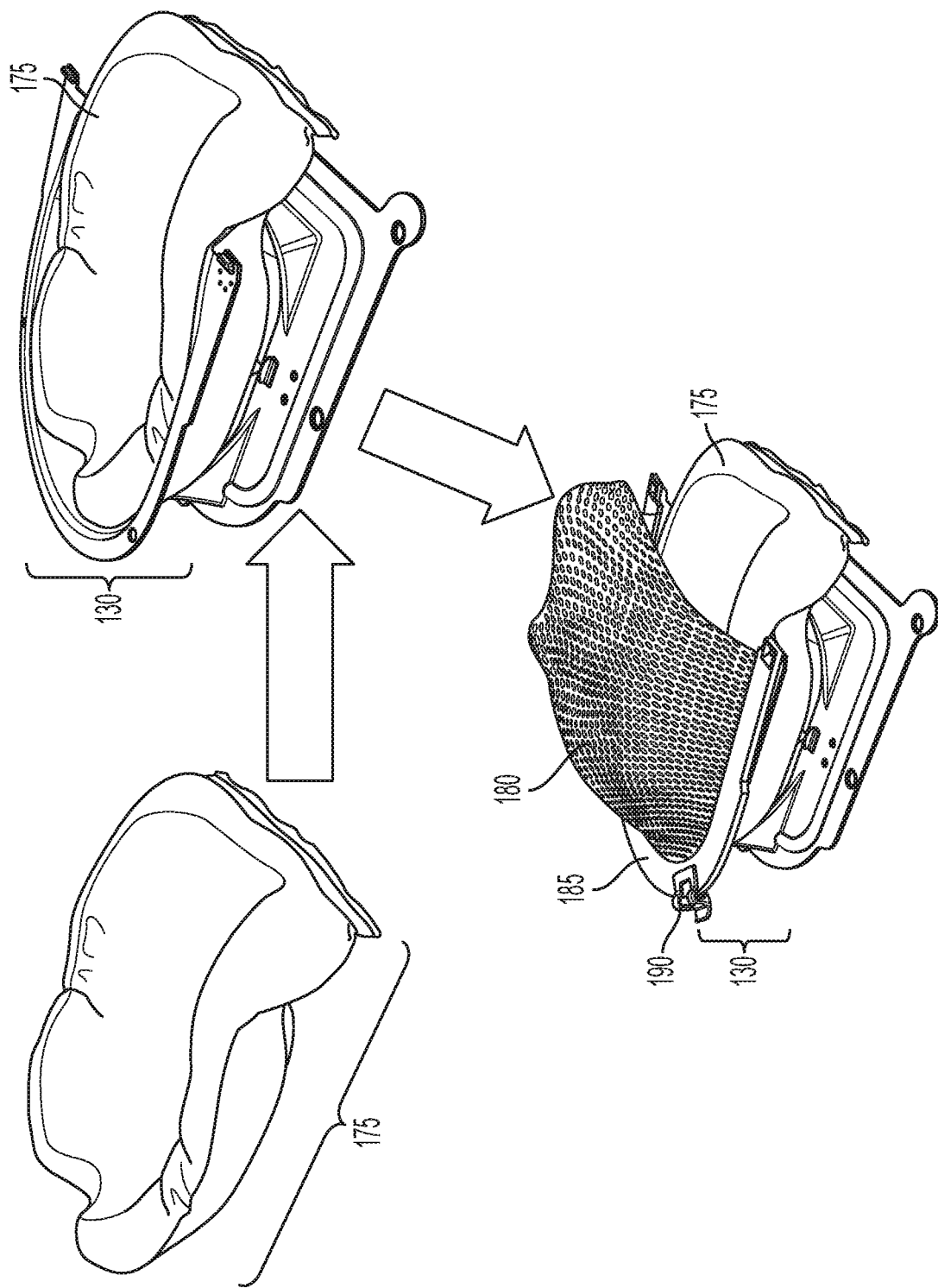

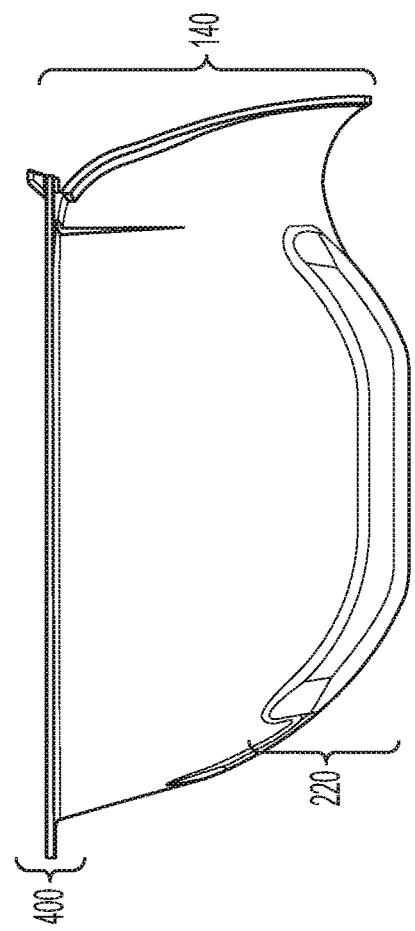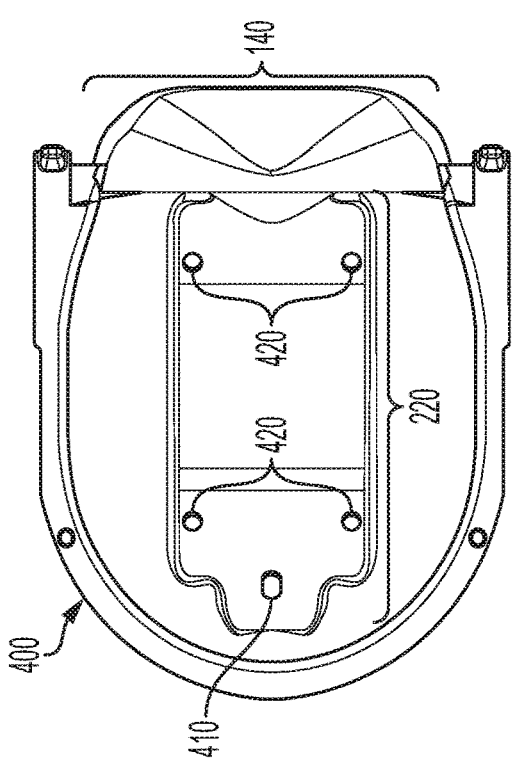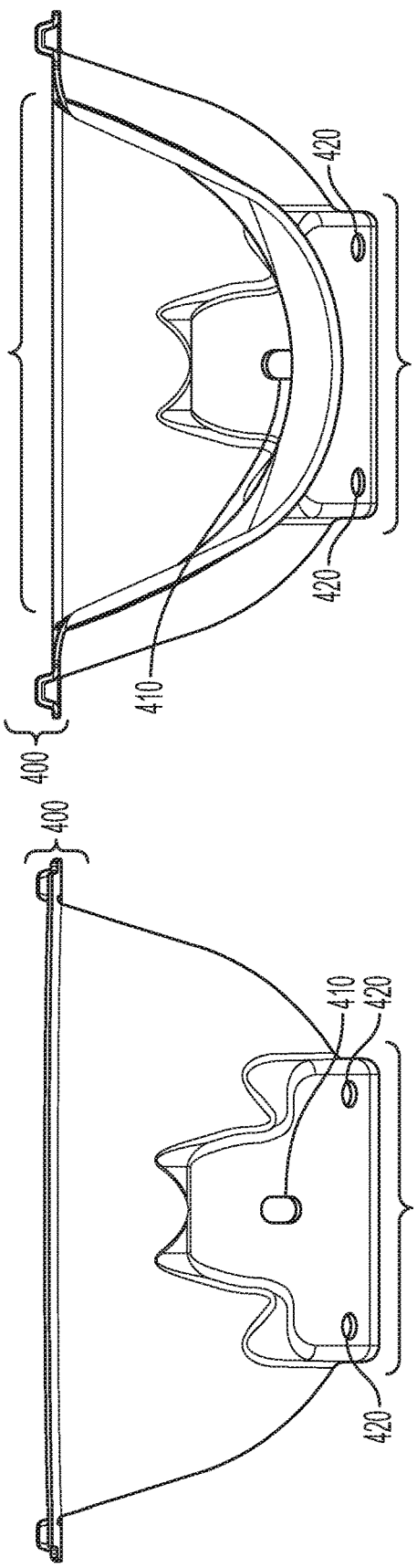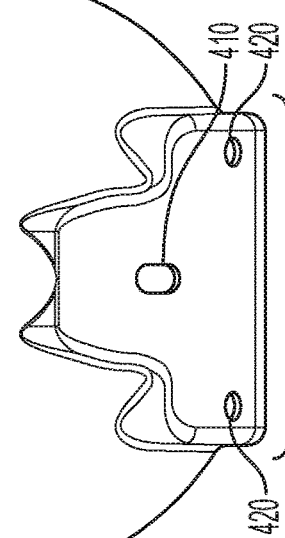

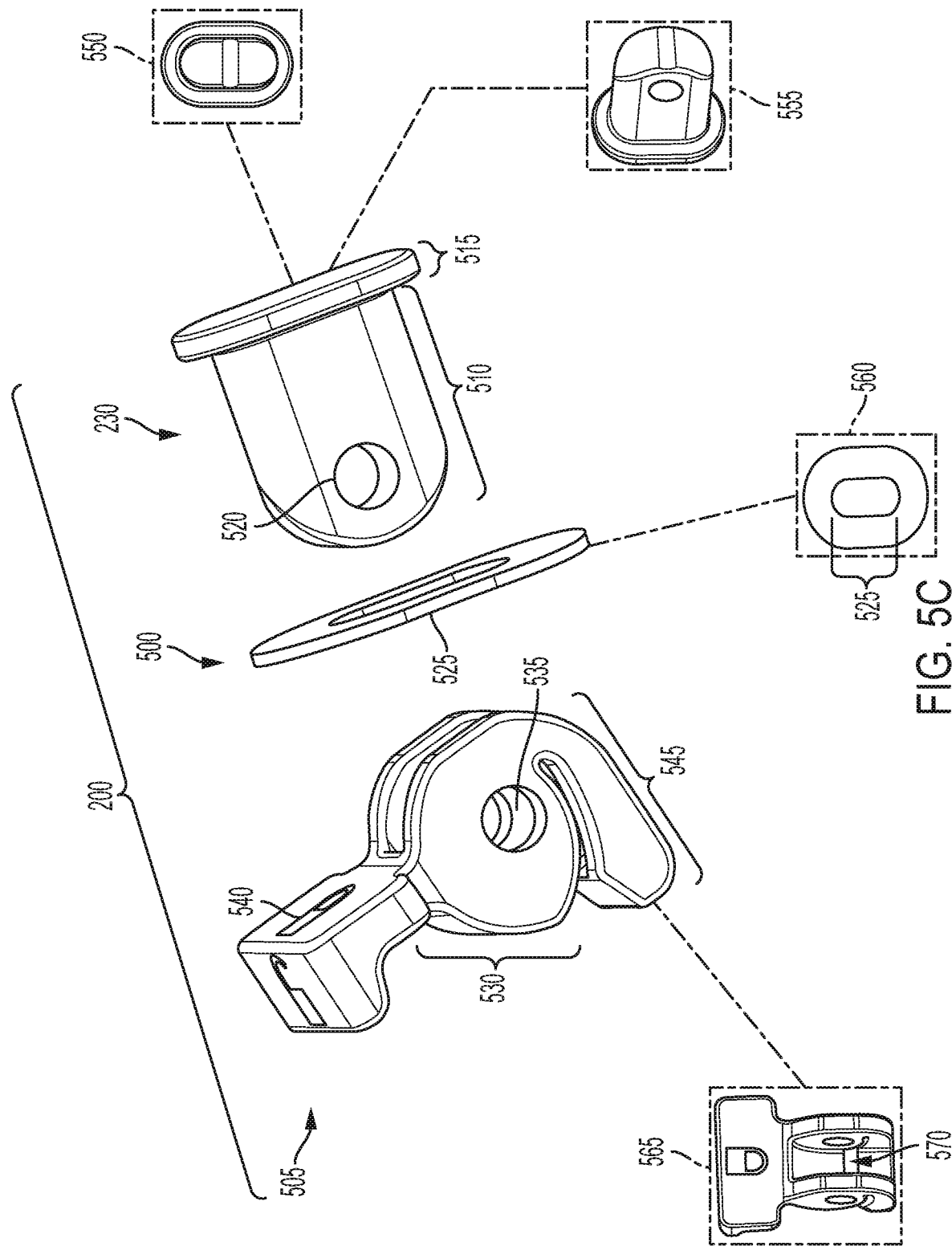

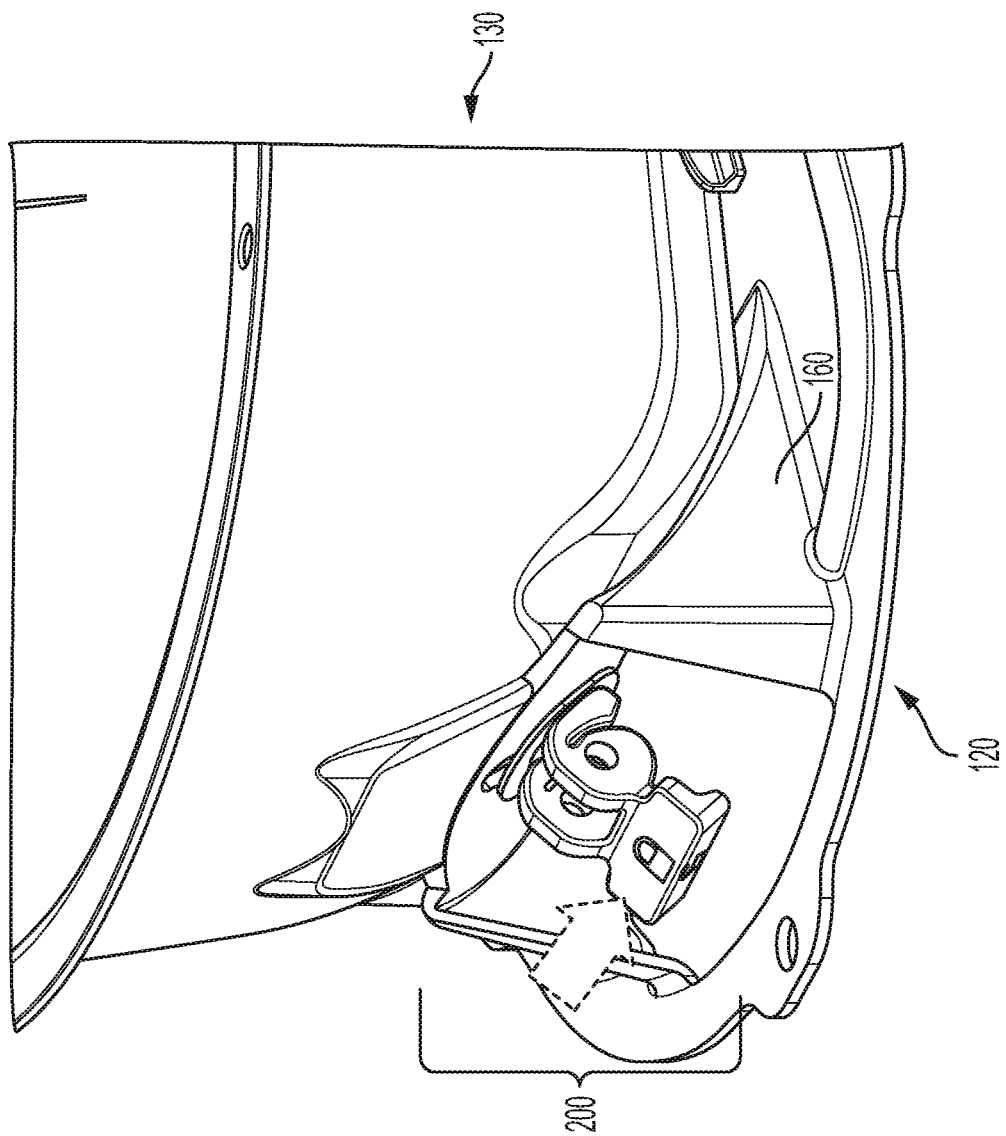

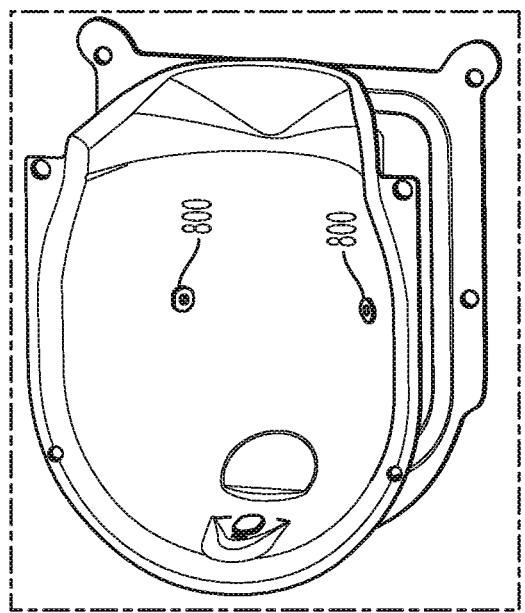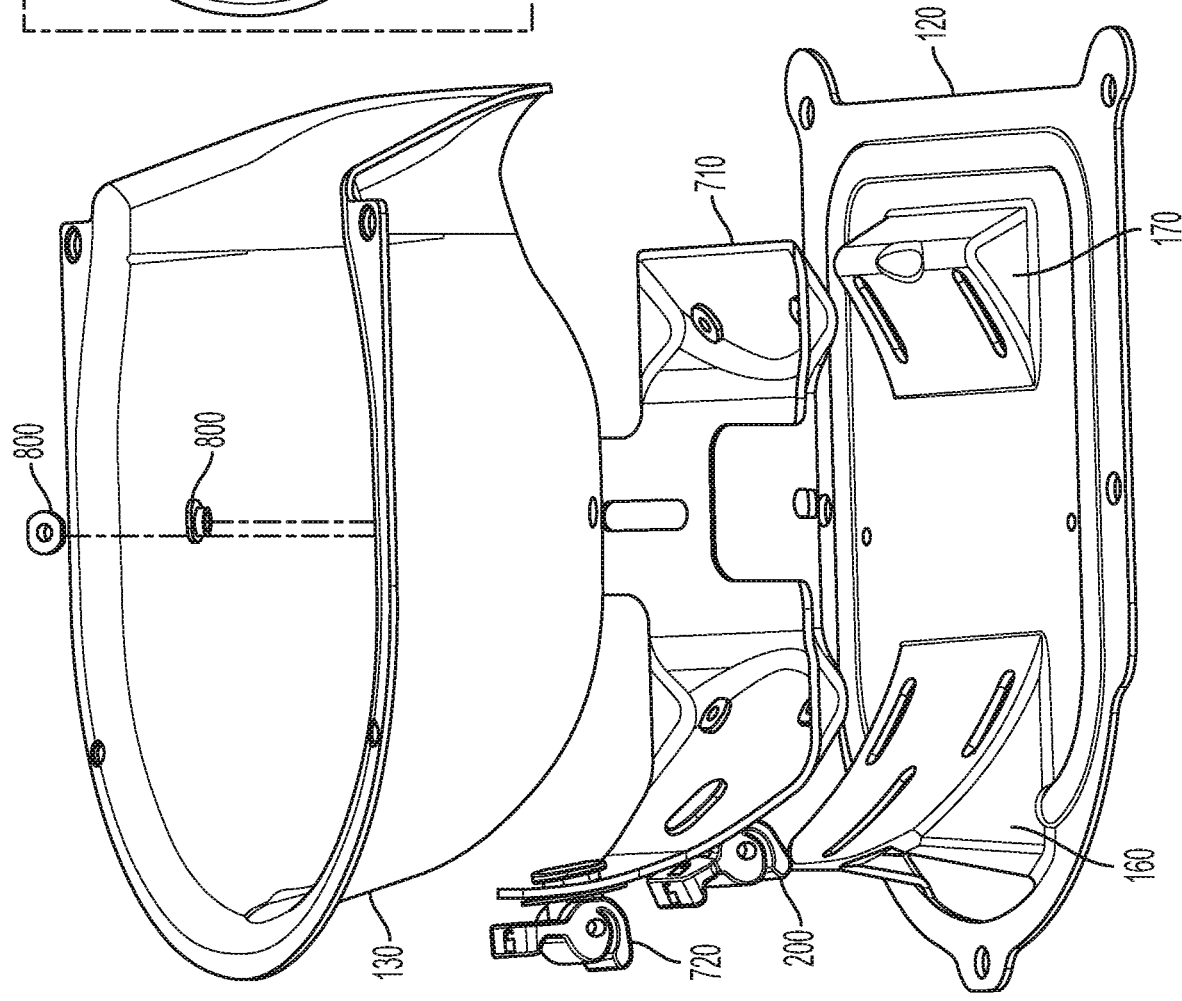
FIG. 8A

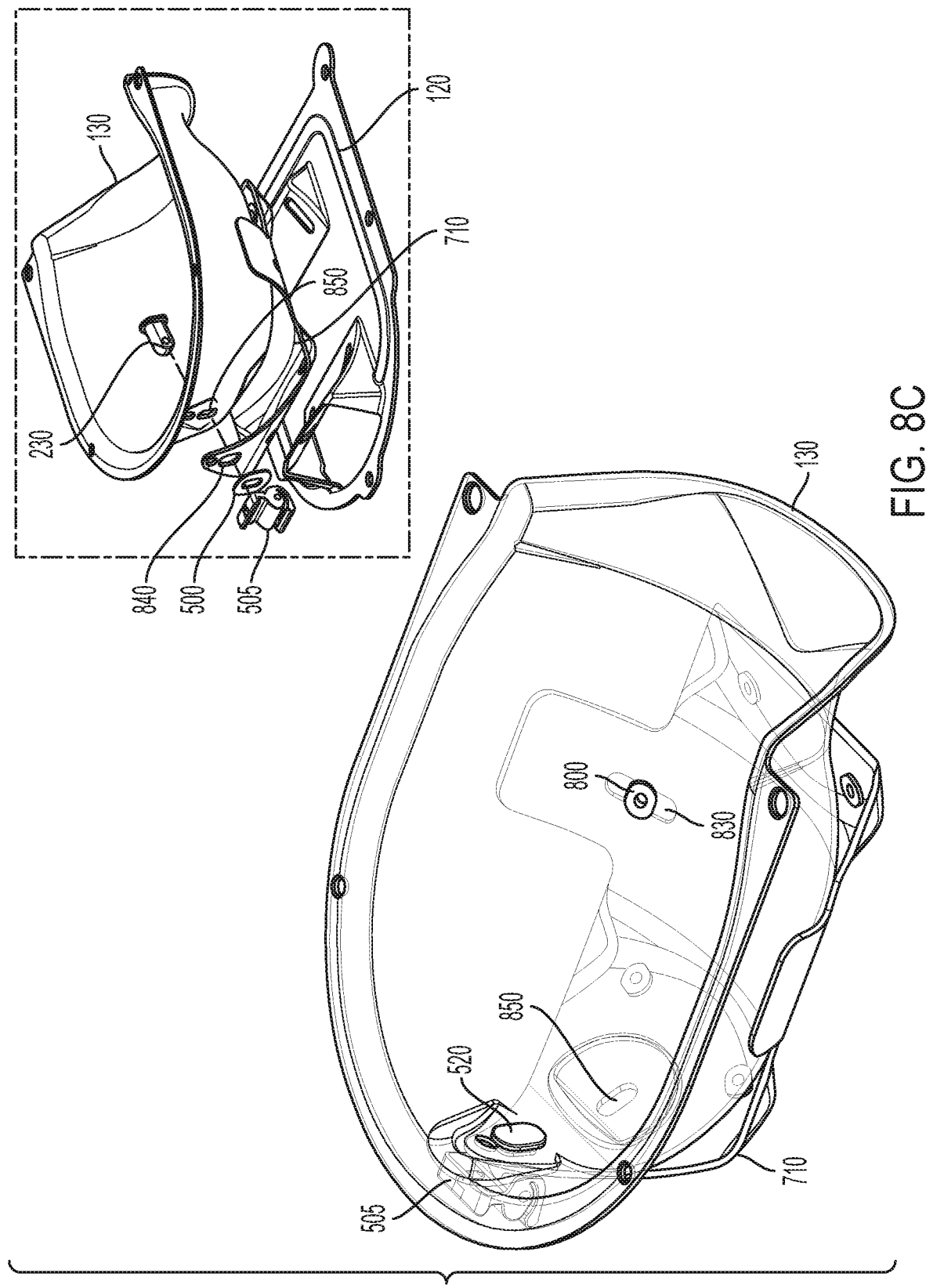

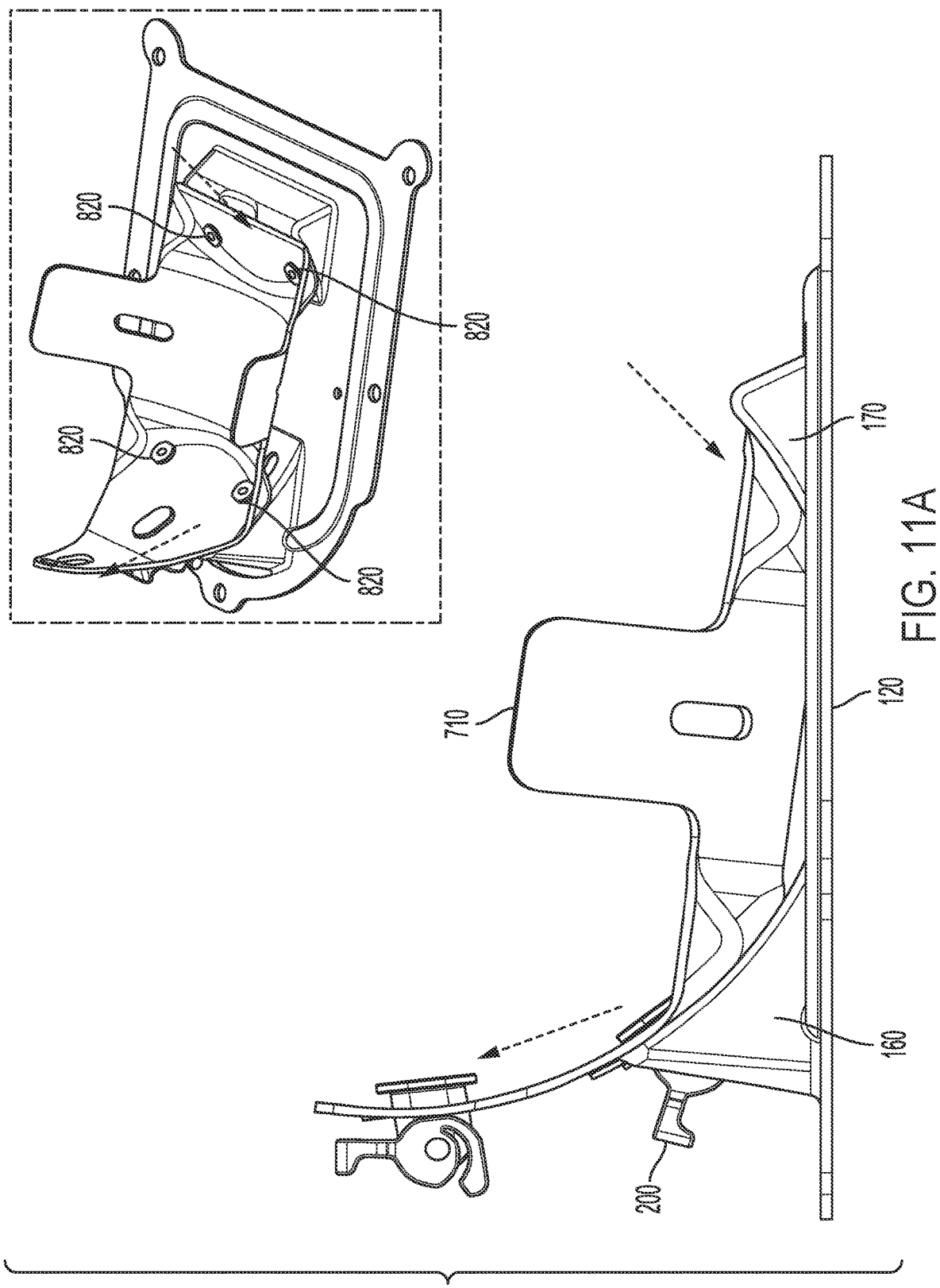

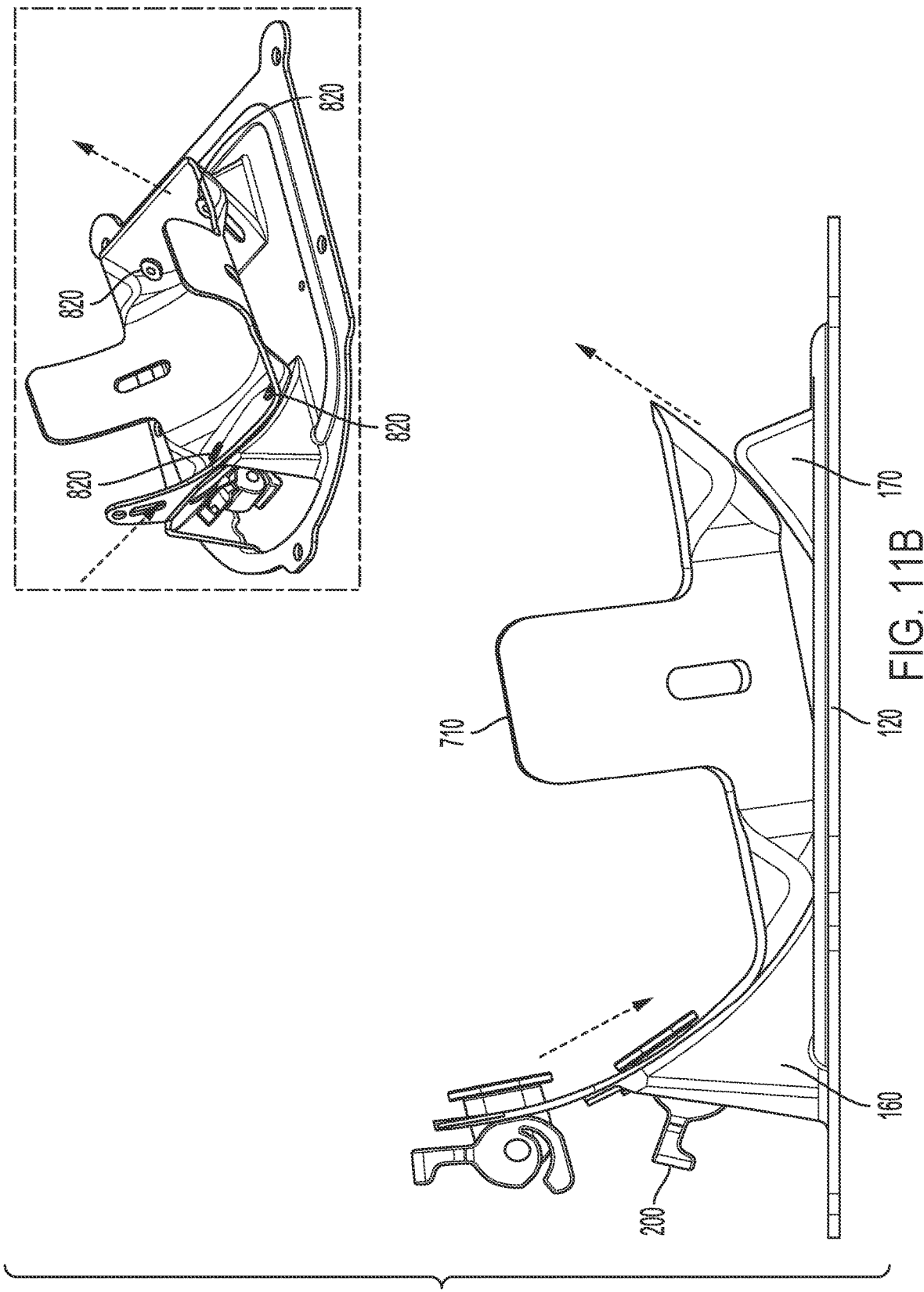

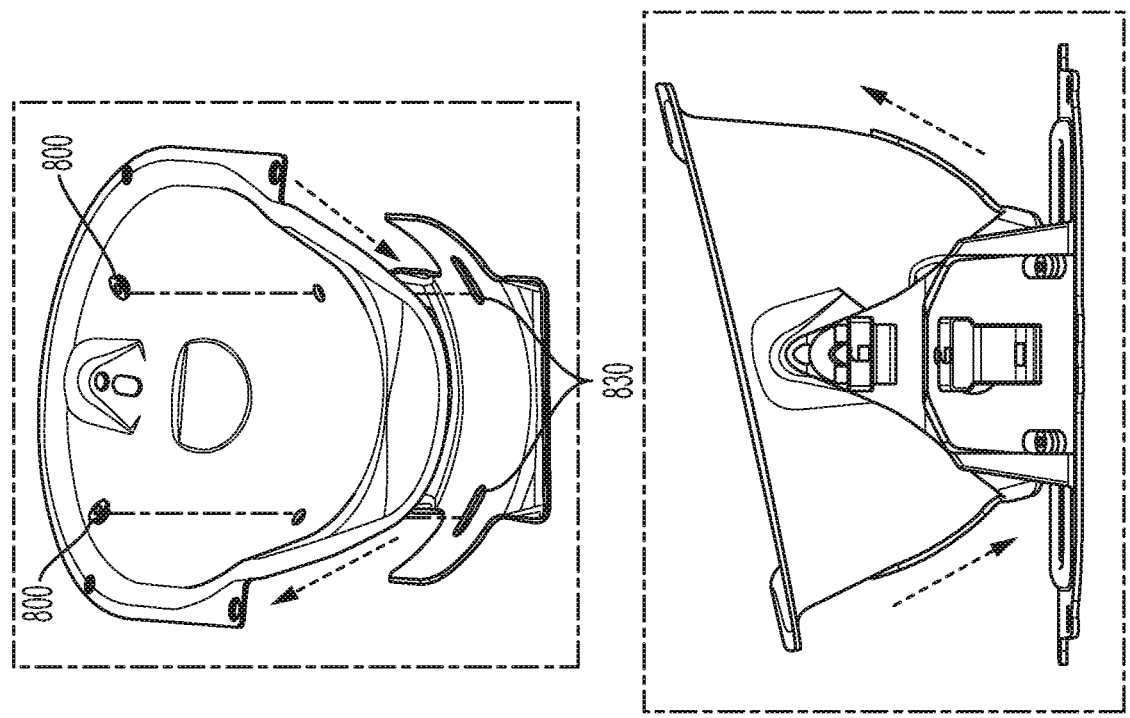
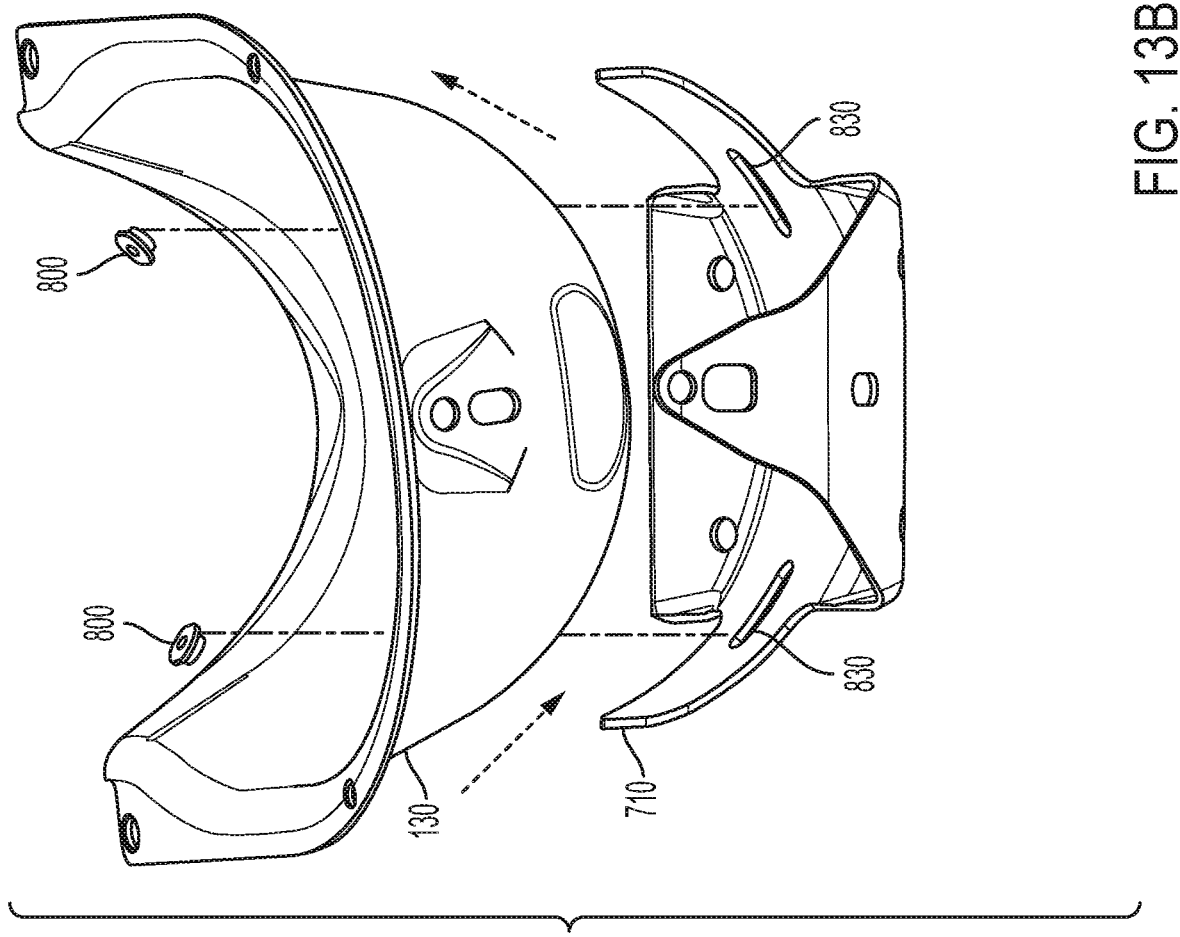
FIG. 13B

BODY PART FIXATION DEVICE WITH PITCH AND/OR ROLL ADJUSTMENT

CROSS-REFERENCE TO RELATED APPLICATION

This application claims priority under 35 U.S.C. § 119, based on U.S. Provisional Application No. 62/460,389, filed Feb. 17, 2017, the disclosure of which is hereby incorporated by reference herein.

BACKGROUND

Certain types of medical treatments require that a portion of a human body be held in a same position to facilitate performance of the medical treatment upon that portion of the body. For example, when brain cancer patients undergo radiation treatment, their heads must be maintained in a precise, repeatable location for the treatment such that the underlying position of the brain tumor is fixed in space for the duration of the radiation treatment or treatments. Various different techniques have been used in the field of radiation oncology for holding body parts in a fixed position.

BRIEF DESCRIPTION OF THE DRAWINGS

FIGS. 1A-1F depict views of an exemplary embodiment in which a body part immobilization device is configured to immobilize a head of a patient;

FIGS. 4A-4D depict four different views of the shell frame of FIG. 1A, including a top view in FIG. 4A, a side view in FIG. 4B, a rear view in FIG. 4C, and a front view in FIG. 4D;

FIGS. 5A-5E depict details of an exemplary embodiment of the pitch adjustment mechanism of FIG. 2A;

FIG. 8A depicts an exploded three-dimensional view of the body part immobilization device of FIG. 7;

FIG. 8C is a three-dimensional view of the components of the body part immobilization device of FIG. 7 that are involved in adjustment of the roll of the shell frame;

FIGS. 11A and 11B depict adjustment of the pitch of the shell frame carriage and the shell frame of the device of FIG. 7;

FIGS. 13A and 13B depict adjustment of the roll of the shell frame relative to the shell frame carriage and the support base of the device of FIG. 7.

DETAILED DESCRIPTION OF THE PREFERRED EMBODIMENTS

Figure 1A:
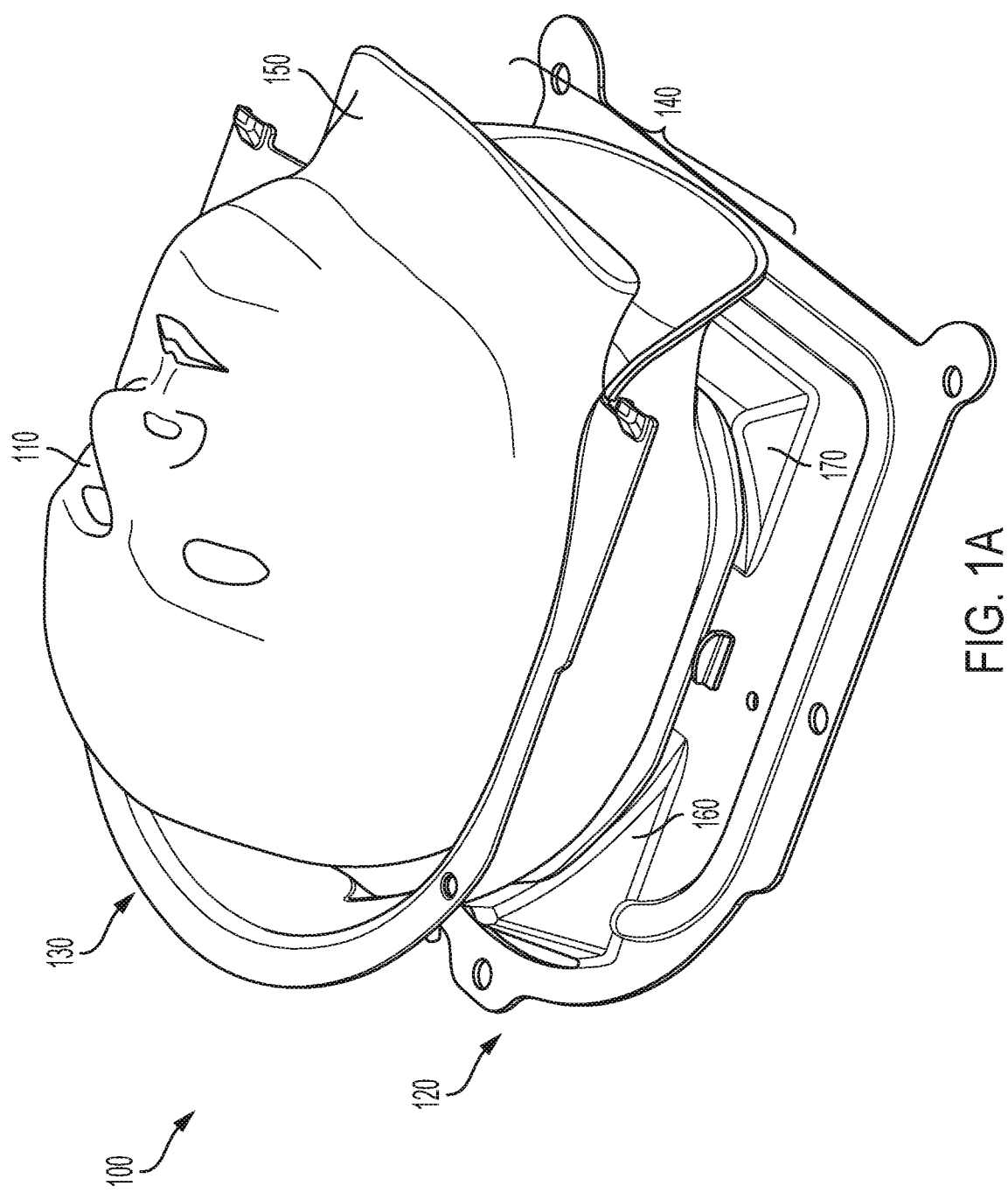
Figure 1B:
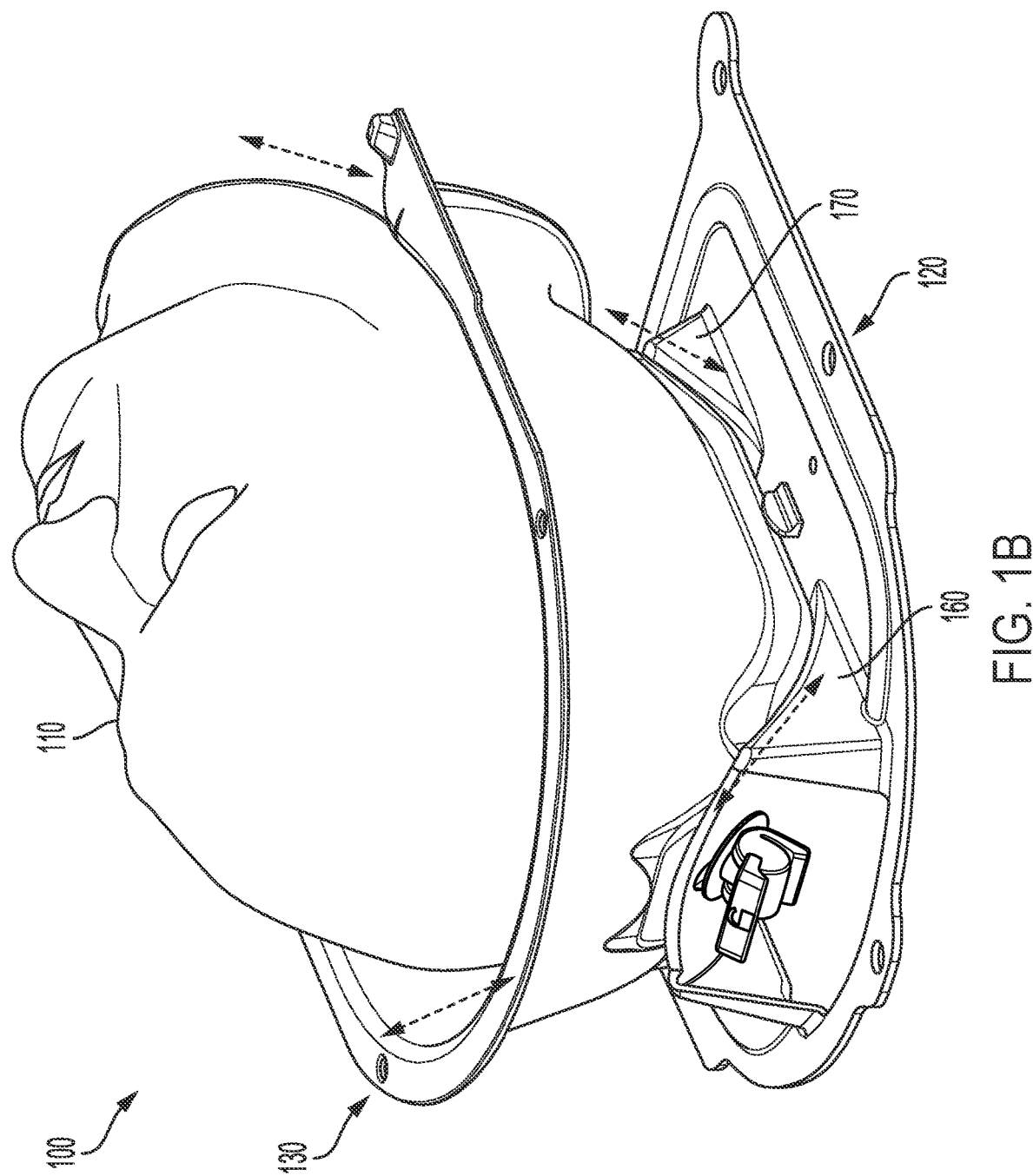
Figure 1D:
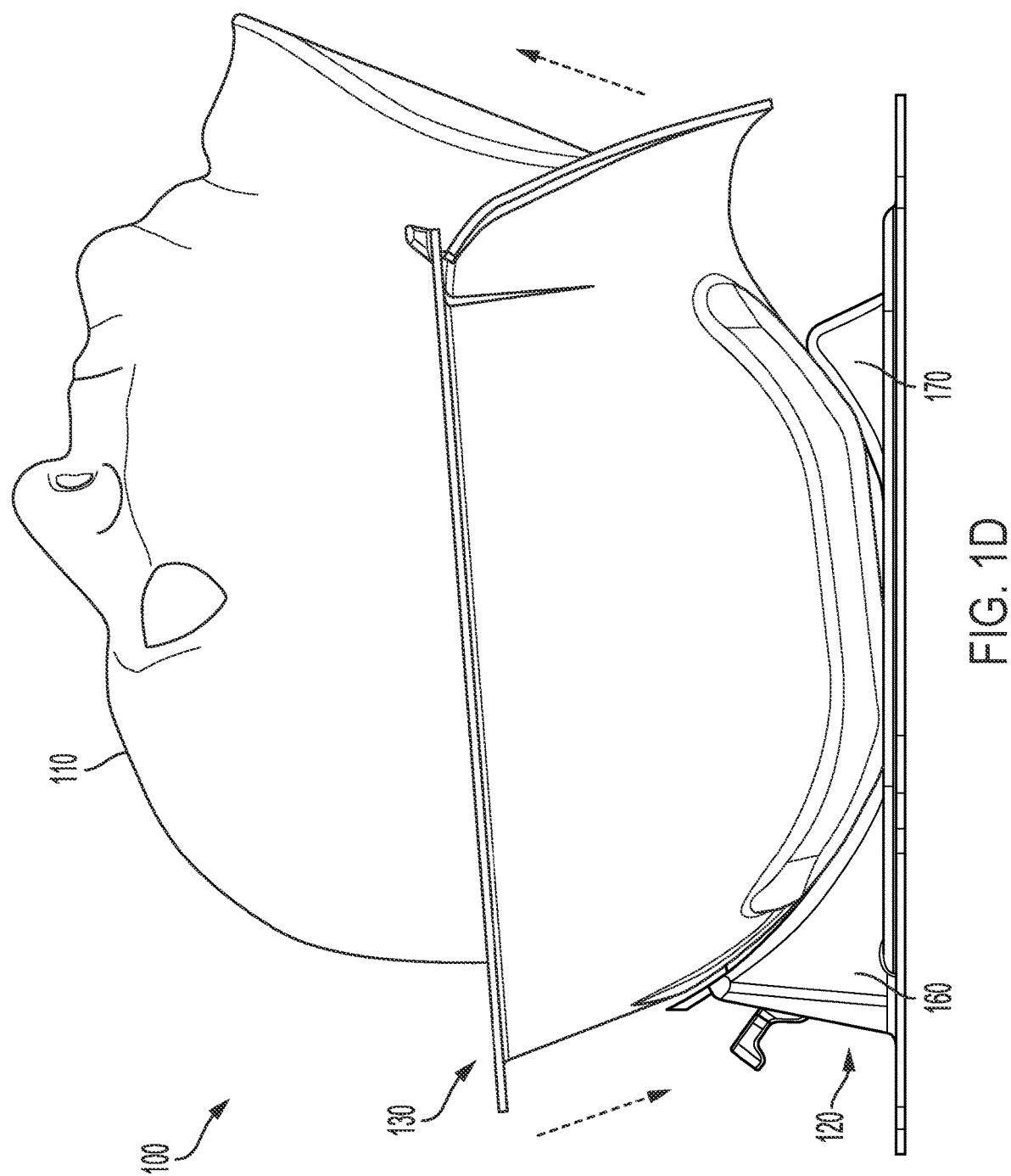

The following detailed description refers to the accompanying drawings. The same reference numbers in different drawings may identify the same or similar elements. The following detailed description does not limit the invention.

A technique, in the field of radiation oncology, for holding body parts in a fixed position uses heat-formable structures that include a sheet of retention material that is stretched over the body part of the patient. For example, for performing radiation treatment of a brain tumor, the heat-formable structure includes a mask having a sheet of retention material that is stretched over the patient's face. To form the mask over the patient's face, a hot water bath or oven may be first used to heat the material of the heat-formable structure such that the sheet of material becomes pliable and deformable. The heat-formable mask is then stretched over the patient's face, and the mask is allowed to cool and harden, permanently forming the mask to the shape of the face of the patient. As an example, a mask having a sheet of thermoplastic retention material, after heating, may be stretched over a patient's face, and then allowed to cool. Upon cooling, the mask, formed to the patient's face, creates a structure that can be used to hold the patient's head in a fixed position during radiation treatments.

After the sheet of thermoplastic retention material of the mask is stretched over the body part of the patient, a frame portion of the mask is attached to a patient support table using an attachment mechanism. Once attached to the support table, however, existing patient masks cannot correct for the incorrect positioning of the patient's body part. Additionally, when the mask frame is attached to the patient support table, the thermoplastic retention material must be stretched a large distance to reach from an upper surface of the patient body (e.g., the patient's face) part all the way down to the surface of the support table. Stretching the thermoplastic retention material to this extent makes it thinner and less rigid than may be desirable.

Exemplary embodiments described herein relate to a body part immobilization device that includes improvements over existing mask frame support and attachment structures. Exemplary embodiments described herein include a deep shell frame that receives and positions a body part, where the shell has an inner shape that conforms to the shape of the body part being immobilized (e.g., a patient's head). The shell frame additionally may contain a cushion (e.g., head cushion) that is customized to fit the body part of the patient. For example, when the body part is a patient's head, the depth of the shell frame enables the customized cushion to surround the head up to a mid-point of the head, providing a large contact surface area that permits a substantial area of support for the head. The shell frame may additionally include an upper flange that permits "easy on/easy off" attachment of a mask frame to the flange. Docking of the mask frame at the upper flange of the shell frame eliminates the need to stretch the thermoplastic material of the mask all the way down to the support table surface, thereby, enhancing the thickness and rigidity of the mask material.

Exemplary embodiments described herein additionally include a support base, and a pitch adjustment mechanism and/or roll adjustment mechanism that, when coupled to the shell frame, enable a pitch and/or roll of the shell frame to be adjusted relative to the support base. Adjustment of the pitch and/or roll of the shell frame enables a positioning of the body part (e.g., positioning of the head within the immobilization device) to be easily adjusted, to satisfy the positioning requirements of the particular medical test or medical treatment being performed, without having to disconnect the mask frame from the shell frame, or without having to remove the mask frame from the body part being immobilized. The pitch adjustment mechanism and/or the roll adjustment mechanism, as described herein, may include a locking mechanism that locks the pitch and/or the roll of the shell frame relative to the support base. The pitch adjustment mechanism, as further described herein, may also include a calibrated pitch adjustment wheel that operates, in conjunction with pitch adjustment slots or notches formed in a bottom surface of the shell frame, to permit the pitch adjustment to be adjusted in a precise and controlled manner. The precise pitch adjustment is performed, using the pitch adjustment wheel, by performing a "click by click" engagement of teeth of the pitch adjustment wheel with the pitch adjustment slots or notches as the pitch adjust wheel is rotated.

A "mask," as referred to herein, includes any structure having a material (e.g., a thermoplastic material) that can be pulled over any body part of a patient to form fit the material to the body part. In some embodiments, a "mask" enables the body part to be immobilized and held in a specific position using a fastening mechanism(s) that may, or may not, be a component of the mask. Thus, a "mask," as used herein, does not refer solely to a structure for placement over a patient's face or head, but includes any type of structure for placement over any body part, or any portion of the body, of a patient (e.g., a structure that pulls over a pelvis of a patient).

FIGS. 1A-1E depict views of a first exemplary embodiment in which a body part immobilization device 100 is configured to immobilize a head 110 of a patient. As shown in FIG. 1A, immobilization device 100 includes a support base 120 and a shell frame 130. Shell frame 130 may include an approximate half shell structure having an inner surface that is configured to conform to a back of the patient's head and neck. The half shell structure of shell frame 130 has a shape that approximates half of a three-dimensional spheroid, where the half roughly transects a vertical center of the spheroid. Shell frame 130 may include a neck cutout 140 in one side of the shell frame 130 that is configured to conform to the neck 150 of the patient and enables, when the patient's head 110 is laid within shell frame 130, the neck 150 to extend out of the interior of shell frame 130. As shown, support base 120 includes a first pitch shell ramp 160 and a second pitch shell ramp 170 that are disposed on support base 120 opposite one another and at a sufficient distance apart to enable the lower surface of shell frame 130 to rest upon support base 120 between the two pitch shell ramps when in a horizontal, non-pitch adjusted position. Pitch shell ramp 160 and pitch shell ramp 170 include sloping ramps that extend downwards towards a center of support base 120. Shell frame 130 and support base 120 may be formed from various types of materials, including metal, plastic, carbon fiber, or a composite material. Shell frame 130 and support base 120 may each be formed from a same type of material, or a different type of material. For example, support base 120 may be formed from metal, and shell frame 130 may be formed from a composite material.

Figure 1E:
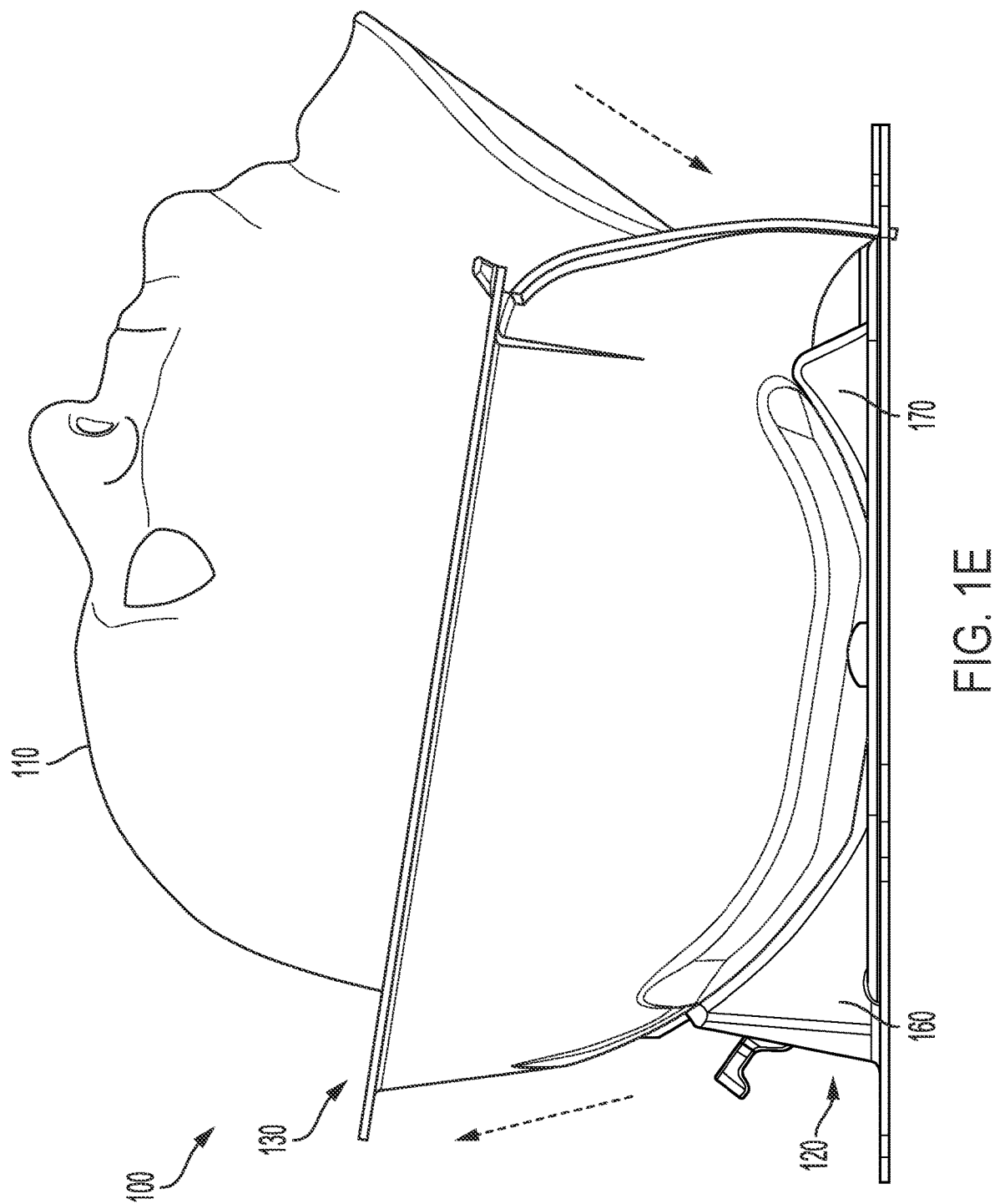

FIGS. 1B-1E depict examples of the adjustment of a pitch of shell frame 130 relative to support base 120. As shown in the three-dimensional view of FIG. 1B, and the one-dimensional side view of FIG. 1C, pitch adjustment involves the movement (i.e., sliding) of a bottom surface of shell frame 130 up an upper surface of pitch ramp 160 (and down an upper surface of pitch ramp 170), or up the upper surface of pitch ramp 170 (and down the upper surface of pitch ramp 160. As further shown in FIG. 1D, movement of the bottom surface of shell frame 130 up pitch ramp 170 causes the side of shell frame adjacent the lower portion of the head 110 of the patient to pitch upwards and the side of the shell frame 130 adjacent the upper portion of the head 110 to pitch downwards. As also shown in FIG. 1E, movement of the bottom surface of shell frame 130 up pitch ramp 160 causes the side of shell frame 130 adjacent the upper portion of the head 110 of the patient to pitch upwards and the side of the shell frame 130 adjacent the lower portion of the head 110 to pitch downwards.

As depicted in FIG. 1F, a head cushion 175 may be placed within shell frame 130 to cushion the patient's head 110 (not shown) against shell frame 130. Given the deep nature of shell frame 130, the head cushion 175 surrounds the head 110 (not shown) up to a top of shell frame 130, thus, providing a large contact surface area and good support for the head 110. With the head 110 supported upon head cushion 175, a mask 180 and mask frame 185 may be docked to shell frame 130 using various fastening mechanisms. In the exemplary embodiment depicted in FIG. 1F, multiple spring clips 190 may be used to fasten mask frame 185 to shell frame 130. The multiple spring clips 190 may be integral to the mask frame 185, may be integral to the shell frame 130, or may be separate and detached items that can be used to fasten mask frame 185 to shell frame 130 when mask frame 185 is docked with shell frame 130.

Figure 2A:
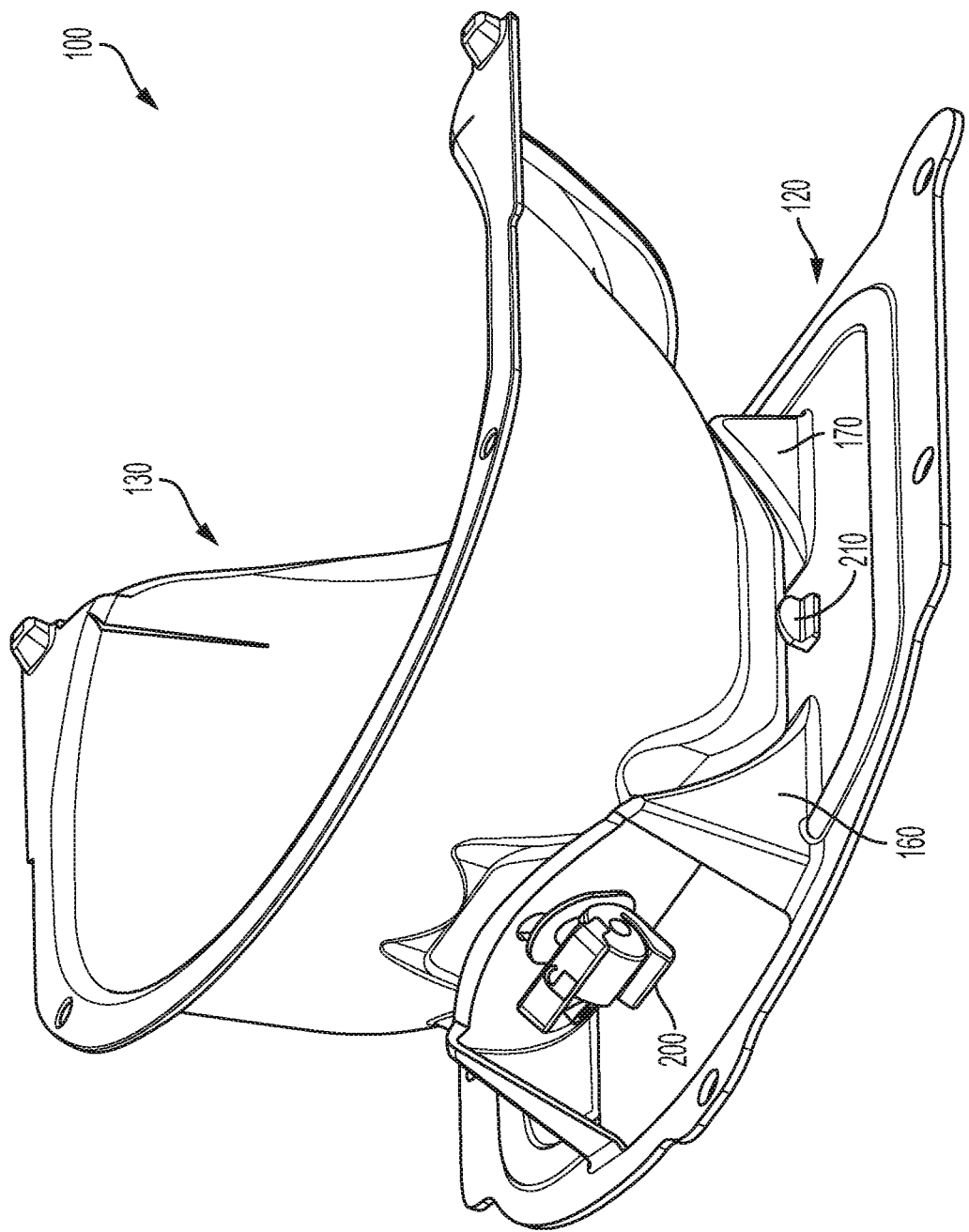
FIGS. 2A-2C depict further details of the pitch adjustment mechanism, and shell frame to support base interface components involved in pitch adjustment of the shell frame, of the immobilization device of FIG. 1A.
Figure 2B:
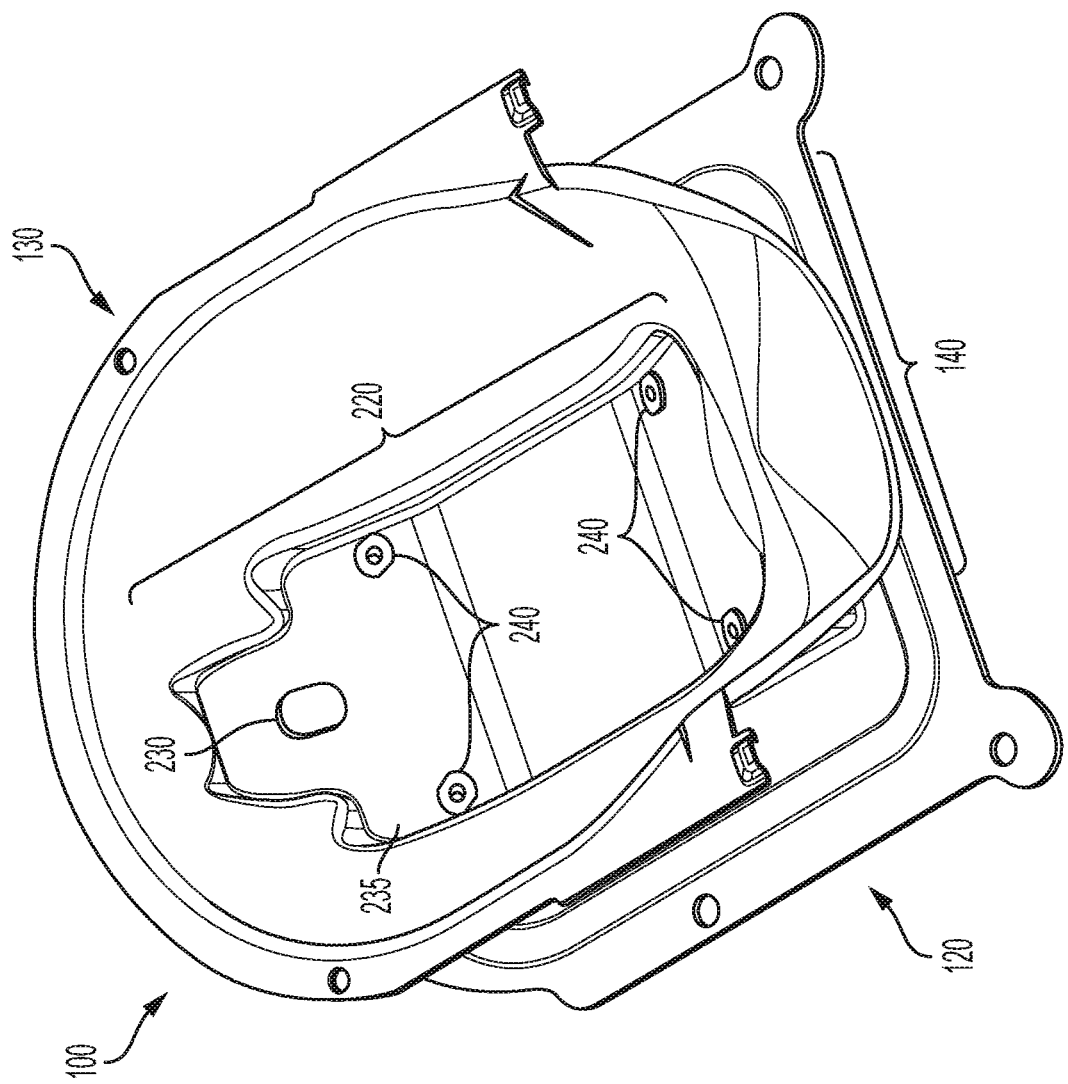
Figure 2C:
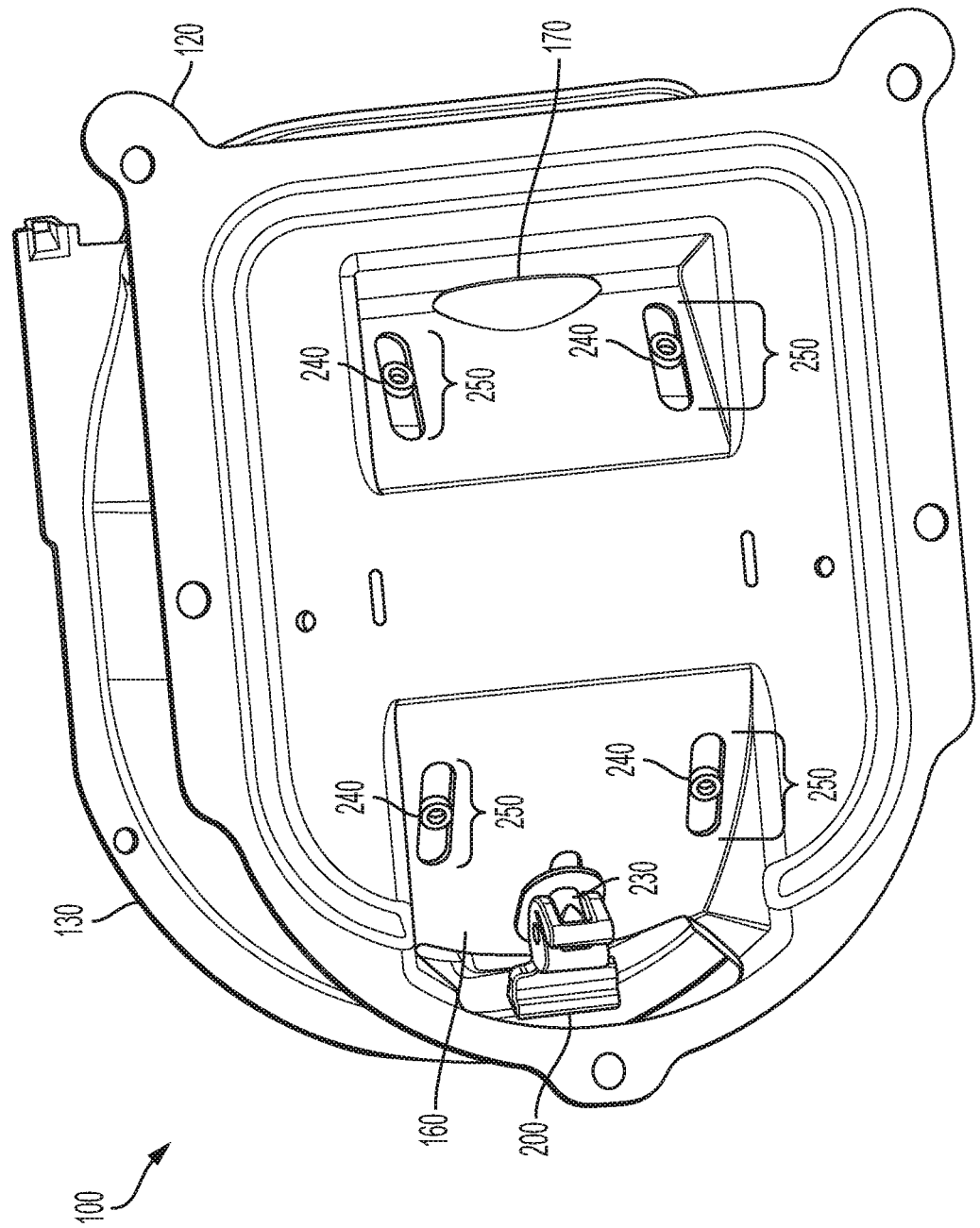

FIGS. 2A-2C depict further details of the pitch adjustment mechanism, and shell frame 130 to support base 120 interface components, involved in pitch adjustment of shell frame 130 of the body part immobilization device 100. As shown in FIG. 2A, a pitch adjustment mechanism 200, exemplary details of which are described further below, may be located on an underside of pitch ramp 160 of support base 120. Pitch adjustment mechanism 200 controls the adjustment of the pitch of shell frame 130 relative to support base 120. As shown in FIG. 2A, shell frame 130 rests in contact with support base 120 in a nominal horizontal position in which a center line of shell frame 130 is equidistant between pitch ramps 160 and 170. A channel retention tab 210 may mount to support base 120, on each side of shell frame 130 (only one tab 210 depicted in FIG. 2A), to "channel" or restrict movement of shell frame 130 by preventing sideways movement and permitting movement in a single dimension that includes movement up or down either of pitch ramps 160 and 170. In other embodiments, other guide structures may be used in lieu of channel retention tabs 210, such as ribs or rails formed into an upper surface of support base 120 between pitch ramps 160 and 170.

FIGS. 2B and 2C depict the shell frame 130 to support base 120 interface components involved in pitch adjustment of shell frame 130. As shown in FIG. 2B, an upper flange of an adjustment fastener 230 of the pitch adjustment mechanism 200 rests against an upper surface within a lower point within the shell frame 130, where the adjustment fastener 230 extends through the shell frame 130 into the support base 120 below. Shell movement pins 240 include upper flanges that rest against the upper surface at multiple locations within the shell of shell frame 130. Shell movement pins 240 extend through shell frame 130 into shell movement slots (not shown in FIG. 2B) of support base 120. Referring to FIG. 2C, shell movement pins 240 are depicted as extending through shell frame 130 into shell movement slots 250 located within pitch ramps 160 and 170 of support base 120. Shell movement slots 250 permit movement of shell movement pins 240 such that shell frame 130 can move up and/or down pitch ramps 160 and 170 via use of pitch adjustment mechanism 200.

FIGS. 2A-2C show immobilization device 100 as including a pitch adjustment mechanism 200 for use in adjusting a pitch of shell frame 130 relative to support base 120, with further details of an exemplary embodiment of pitch adjustment mechanism 200 being shown below with respect to FIGS. 5A-5E. However, in another implementation, pitch adjustment mechanism 200 may be removed from immobilization device 100 such that there is no pitch adjustment mechanism 200 for use in adjusting the pitch of shell frame 130. In this implementation, a user may merely apply manual force to shell frame 130 to cause the pitch of shell frame 130 to change relative to support base 120, without having to use any type of pitch adjustment mechanism 200. Furthermore, in this implementation, shell movement pins 240 may include lower flanges (or other means of retaining shell movement pins 240 within shell movement slots 250), in addition to upper flanges, that retain shell frame 130 within shell movement slots 250 such that shell frame 130 and shell movement pins 240 do not easily come out of shell movement slots 250.

Though not depicted in FIGS. 2A-2C, immobilization device 100 may additionally include pitch adjustment reference markers located upon either support base 120 and/or shell frame 130 that enable a visual inspection of a quantifiable amount of how much the pitch of shell frame 130 has been adjusted in either direction (i.e., up or down). These pitch adjustment reference markers, therefore, enable accurate and precise adjustments of the pitch of shell frame 130 to be made using a visual inspection. In one implementation, the pitch adjustment reference markers may be included upon a sticker that is applied at an appropriate location upon either support base 120 or shell frame 130 to show how much pitch has been applied to shell frame 130. In another implementation, the pitch adjustment reference marks may be applied along a side surface of pitch ramp 160, and correspondingly along a lower side surface of shell frame 130. Thus, movement of the pitch adjustment reference marks applied to the lower side surface of shell frame 130 relative to pitch adjustment reference marks applied to the side surface of pitch ramp 160, as the pitch of shell frame 130 is adjusted, enable a visual inspection to ascertain an amount of pitch applied to shell frame 130 relative to support base 120. Other locations upon shell frame 130 and/or support base 120 may be used for applying pitch adjustment reference markers.

Figure 3B:
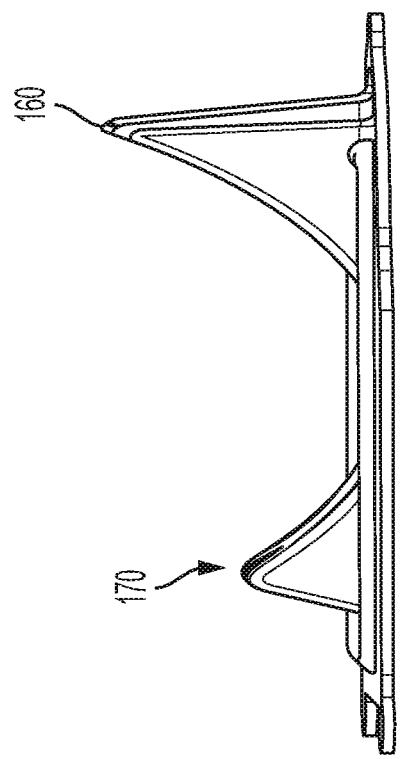
FIGS. 3A-3D depict four different views of the support base of FIG. 1B, including a top view in FIG. 3A, a side view in FIG. 3B, a rear view in FIG. 3C, and a front view in FIG. 3D.
Figure 3D:
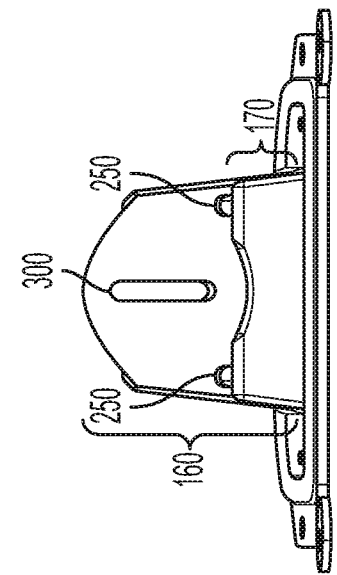
Figure 3A:
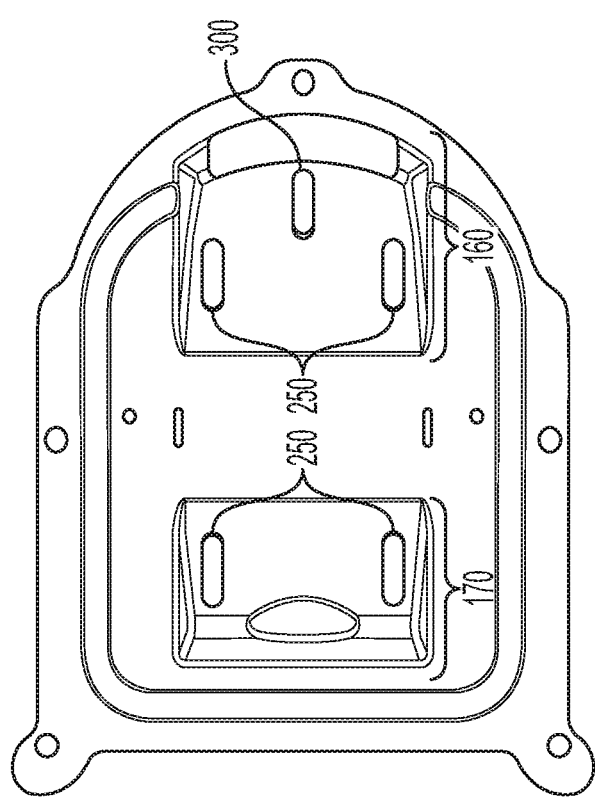
Figure 3C:
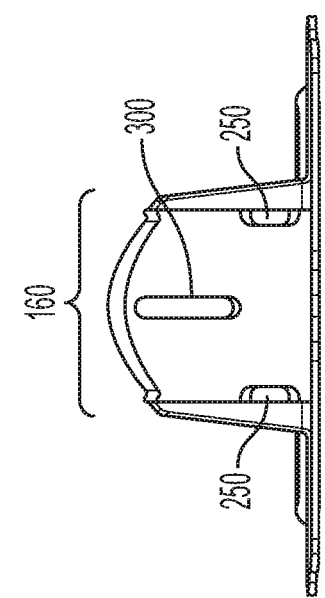

FIGS. 3A-3D depict four different views of support base 120, including a top view in FIG. 3A, a side view in FIG. 3B, a rear view in FIG. 3C, and a front view in FIG. 3D. As can be seen in the views of FIGS. 3A and 3B, a roughly flat and planar lower member of support base 120 connects to opposing pitch ramps 160 and 170. Rearward pitch ramp 160 may have approximately twice the height of forward pitch ramp 170, and each of pitch ramps 160 and 170 may have concave inner ramps that extend from the planar lower member of support base 120 to a top of pitch ramps 160 and 170. Pitch ramps 160 and 170 may be formed integrally to support base 120 (i.e., formed from the same material and formed as a single structure), or may be formed as separate components, and then connected to support base 120 (e.g., snapped into place upon support base 120). As shown in FIG. 3C, a pitch adjustment slot 300 extends through pitch ramp 160, and is approximately centered upon the concave inner surface of pitch ramp 160. Pitch adjustment slot 300 extends a certain length down the concave inner surface of pitch ramp 160 and sets the maximum adjustment distance that the pitch of shell frame 130 may be adjusted. As can further be seen in FIG. 3C, two shell movement slots 250 extend through pitch ramp 160, and are located towards each outer edge of pitch ramp 160 and towards a lower portion of the concave inner surface of pitch ramp 160. FIG. 3D further depicts pitch ramp 160 from an opposite side to that shown in FIG. 3C. In this front view, pitch adjustment slot 300 and shell movement slots 250 are shown extending through the concave inner surface of the pitch ramp 160. A rear of pitch ramp 170 can further be seen in FIG. 3D.

FIGS. 4A-4D depict four different views of shell frame 130 of device 100, including a top view in FIG. 4A, a side view in FIG. 4B, a rear view in FIG. 4C, and a front view in FIG. 4D. As can be seen in the views of FIGS. 4A-4D, shell frame 130 includes a half shell structure having an inner surface that is configured to conform to a back of the patient's head and neck. The half shell structure of shell frame 130 has a shape that approximates half of a three-dimensional spheroid, where the half roughly transects a center of the spheroid. Shell frame 130 may include a neck cutout 140 in one side of the shell frame 130 that includes an opening in the half shell that is configured to conform to the neck 150 of the patient and enables, when the patient's head 110 is laid within shell frame 130, the neck 150 to extend out of the interior of shell frame 130 through the neck cutout 140.

As shown in FIGS. 4A-4D, an upper edge of shell frame 130 includes a flange 400 that extends around a perimeter of the upper edge of the shell frame 130. The flange extends approximately ½ to ¾ of an inch out from the upper edge of shell frame 130. As can further be seen in FIGS. 4A-4D, a recessed pitch foot 220 is formed in a lower surface of shell frame 130. Pitch foot 220 includes a roughly rectangular recess (as seen from the top view of FIG. 4A) formed in the lower surface of shell frame 130 that serves as the "foot" of the shell frame 130 that rests upon the pitch ramps 160 and 170 of the underlying support base 120 (not shown in FIGS. 4A-4D). The pitch foot 220 "wraps" around the convex lower surface of shell frame 130 and may be centered about a first center line that extends side-to-side through shell frame 130 and may be centered about a second center line that extends front-to-back through shell frame 130.

As further seen in FIGS. 4A-4D, pitch foot 220 further includes a pitch adjustment fastener retention hole 410 and multiple shell movement pin retention holes 420. Pitch adjustment fastener retention hole 410 retains a pitch adjustment fastener (described below) of the pitch adjustment mechanism 200, where the pitch adjustment fastener extends through retention hole 410, and through pitch adjustment slot 300 in support base 120. Further details of the exemplary pitch adjustment mechanism 200 are described below with respect to FIGS. 5A-5E. Shell movement pin retention holes 420 retain shell movement pins 240 (shown in FIGS.

2B and 2C) that extend through retention holes 420, and through shell movement slots 250 (shown in FIG. 2C) in the pitch ramps 160 and 170 of support base 120. Shell movement pins 240 (not shown in FIGS. 4A-4D) each include an upper flange that rests against the inner surface of shell frame 130 within pitch foot 220. The upper flange of each shell movement pin 240, in combination with the retention hole 420 each pin extends through, hold each shell movement pin 240 in place within shell frame 130.

Figure 4E:
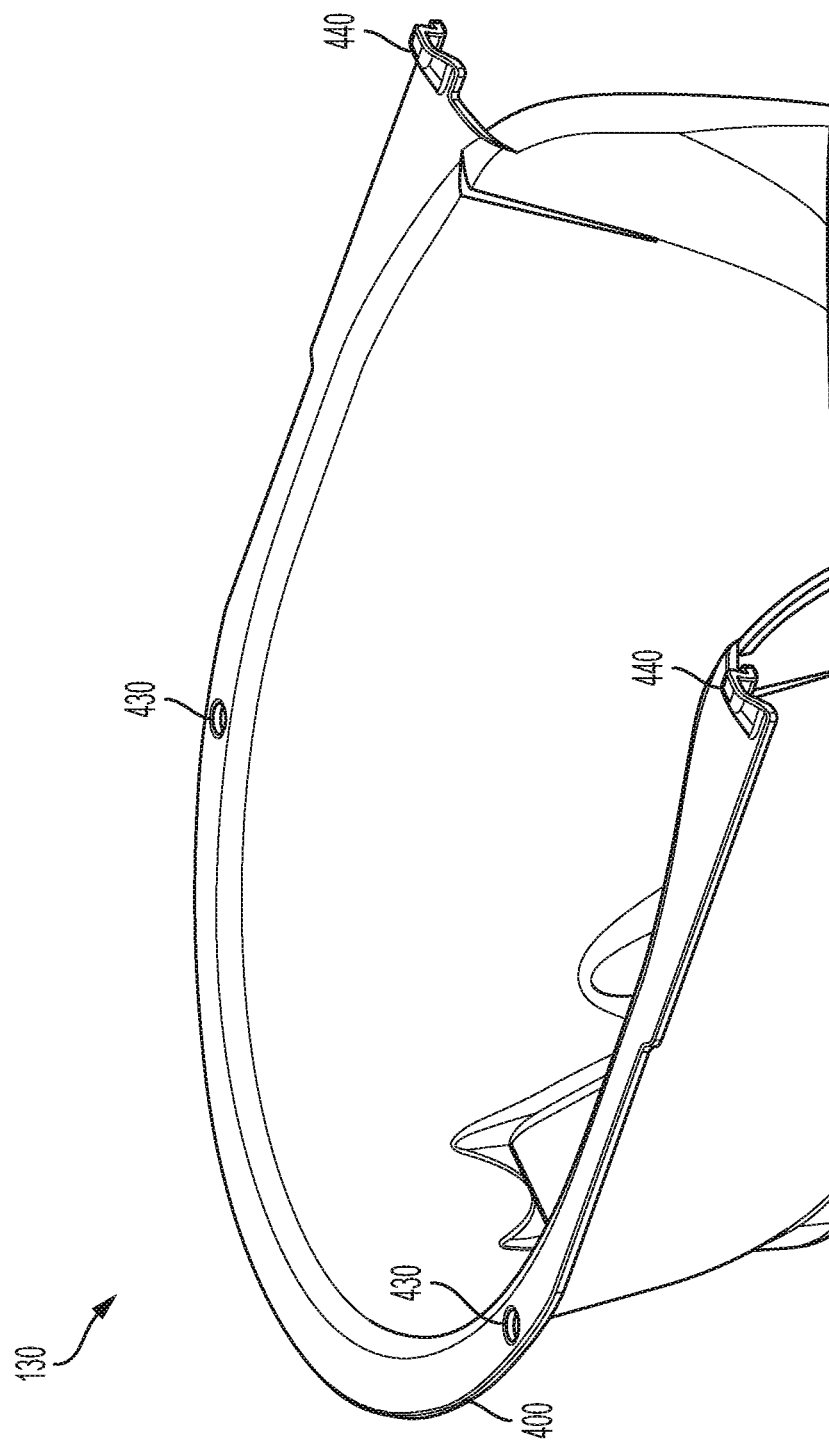
FIG. 4E depicts further exemplary details of the flange of the shell frame of FIG. 1A.

FIG. 4E depicts further exemplary details of flange 400 of shell frame 130. As shown, an upper surface of flange 400 includes multiple registration holes 430, and multiple registration tabs 440 for docking a frame of a body part mask (not shown) to shell frame 130. The frame of the body part mask (not shown) may include multiple pins, on an underside of the frame, that line up with, and can be inserted into, registration holes 430. The frame of the body part mask (not shown) may further include its own registration holes, which extend through the frame and line up with, and can be inserted over, registration tabs 440. Therefore, when docking the body part mask to shell frame 130, the registration holes 430 and registration tabs 440, ensure the proper positioning of the body part mask relative to shell frame 130.

Figure 5A:
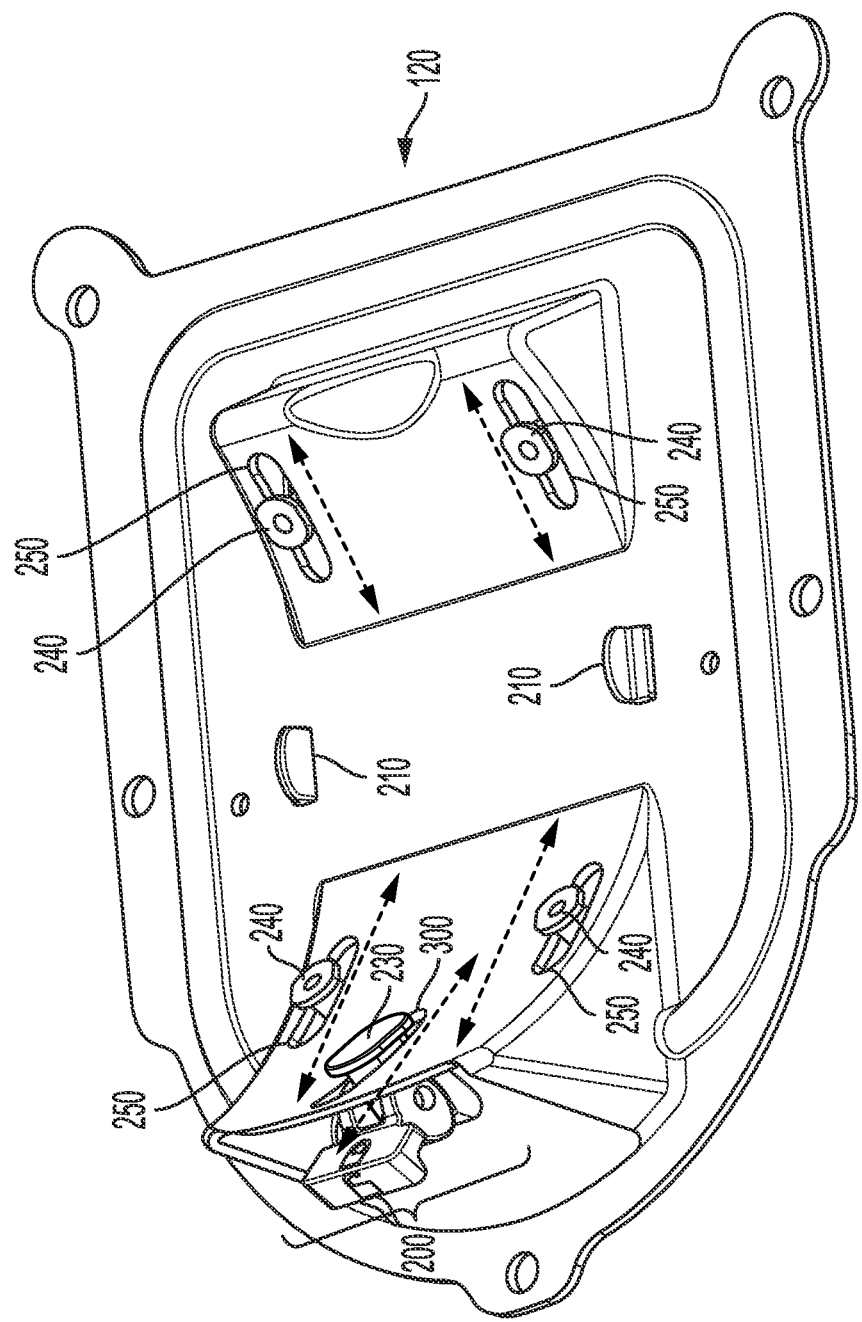
Figure 5B:
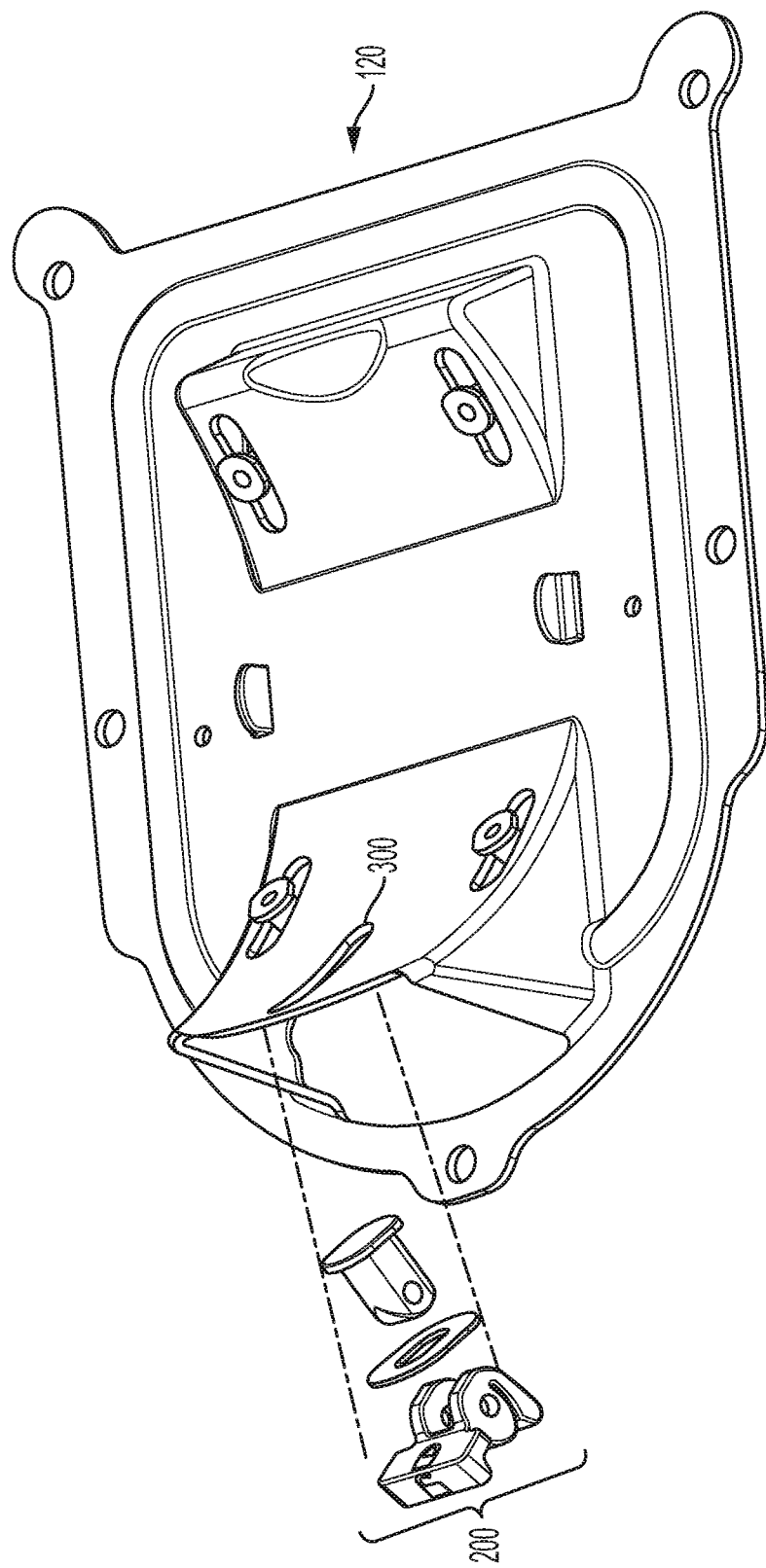

FIGS. 5A-5E depict details of an exemplary embodiment of pitch adjustment mechanism 200. FIG. 5A depicts a view of the overall operation of pitch adjustment mechanism 200, that doesn't show shell frame 130 for purposes of simplicity. As shown, an adjustment fastener 230 of pitch adjustment mechanism 200 extends through pitch adjustment slot 300 of support base 120. Movement of pitch adjustment mechanism 200, to adjust the pitch either to the left or to the right in FIG. 5A, correspondingly causes shell movement pins 240 (which are attached to shell frame 130) to move to the left or to the right in pitch movement slots 250. Movement of shell movement pins 240 within pitch movement slots 250 results in shell frame 130 (not shown in FIG. 5A) moving in a "channel" created by channel retention tabs 210 that prevent any sideways movement of shell frame 130. FIG. 5B illustrates the pitch adjustment mechanism 200 of FIG. 5A in an "exploded view" such that the individual components can be discerned. FIG. 5C further depicts a close up of the "exploded view" of the pitch adjustment mechanism 200 of FIG. 5B. Pitch adjustment mechanism 200, in this embodiment, includes four components, an adjustment fastener 230, a locking spacer 500, an adjustment/locking knob 505, and an adjustment pin (not shown).

Locking spacer 500 includes a spacer hole 525. An additional break out view 560 of locking spacer 500 is depicted in FIG. 5C, showing the size of spacer hole 525 relative to the shape and size of spacer 500. Locking spacer 500 has an oval shape, with an oval shaped spacer hole 525 centered within the oval shape of spacer 500. Locking spacer 500 has a thickness of approximately ⅛ of an inch, and may be formed from various types of materials, such as metal, plastic, carbon fiber, or a composite material. The oval shaped spacer hole 525 has a size that permits insertion of adjustment fastener 230 through spacer hole 525.

Adjustment fastener 230 further includes a fastener body 510, a flange 515, and a fastener pin retention hole 520. Additional break out views 550 and 555 of adjustment fastener 230 are depicted in FIG. 5C, showing the shape of adjustment fastener 230 from different viewing angles. Fastener body 510, as shown in the front break out view 550, has an oval shape for insertion through the oval spacer hole 525 of locking spacer 500. Fastener pin retention hole 520 permits an adjustment pin (not shown) to be inserted into the retention hole 520, as described further below. Flange 515 is disposed at one end of fastener body 510, and pin retention hole 520 is disposed close to another end of fastener body 510. Flange 515 has an oval shape that is larger than the oval shape of fastener body 510, such that flange 515 extends outwardly from the outer surface of fastener body 510.

Adjustment/locking knob 505 further includes an adjustment body 530, a pin retention hole 535, an adjustment knob 540, and a locking extension 545. A break out view 565 of adjustment/locking knob 505 is also depicted in FIG. 5C, showing a fastener slot 570 that receives a portion of fastener body 510 that includes the fastener pin retention hole 520. To combine knob 505, spacer 500 and fastener 230 to create pitch adjustment mechanism 200 (or to create roll adjustment mechanism 720 described below), fastener body 510 is inserted through hole 525 of spacer 500 and into fastener slot 570 such that pin retention hole 535 lines up with pin retention hole 520. The adjustment pin (not shown) can then be inserted through pin retention hole 535 of knob 505 into pin retention hole 520 of fastener 230 such that the adjustment pin can then serve as an "axle" about which the entirety of adjustment/locking knob 505 rotates when force is applied to adjustment knob 540.

Adjustment knob 540 includes, for example, a rectangular touch surface via which force may be applied to cause the rotation of adjustment/locking knob 505. Adjustment knob 540 connects to adjustment body 530, which has a roughly cylindrical shape through which pin retention hole 535 extends on a forward surface, and into which fastener slot 570 extends on a side surface. Locking extension 545 connects to a side surface of adjustment body 530, creating, for example, a reversed "e" shape seen in the main view depicted in FIG. 5C.

Figure 5D:
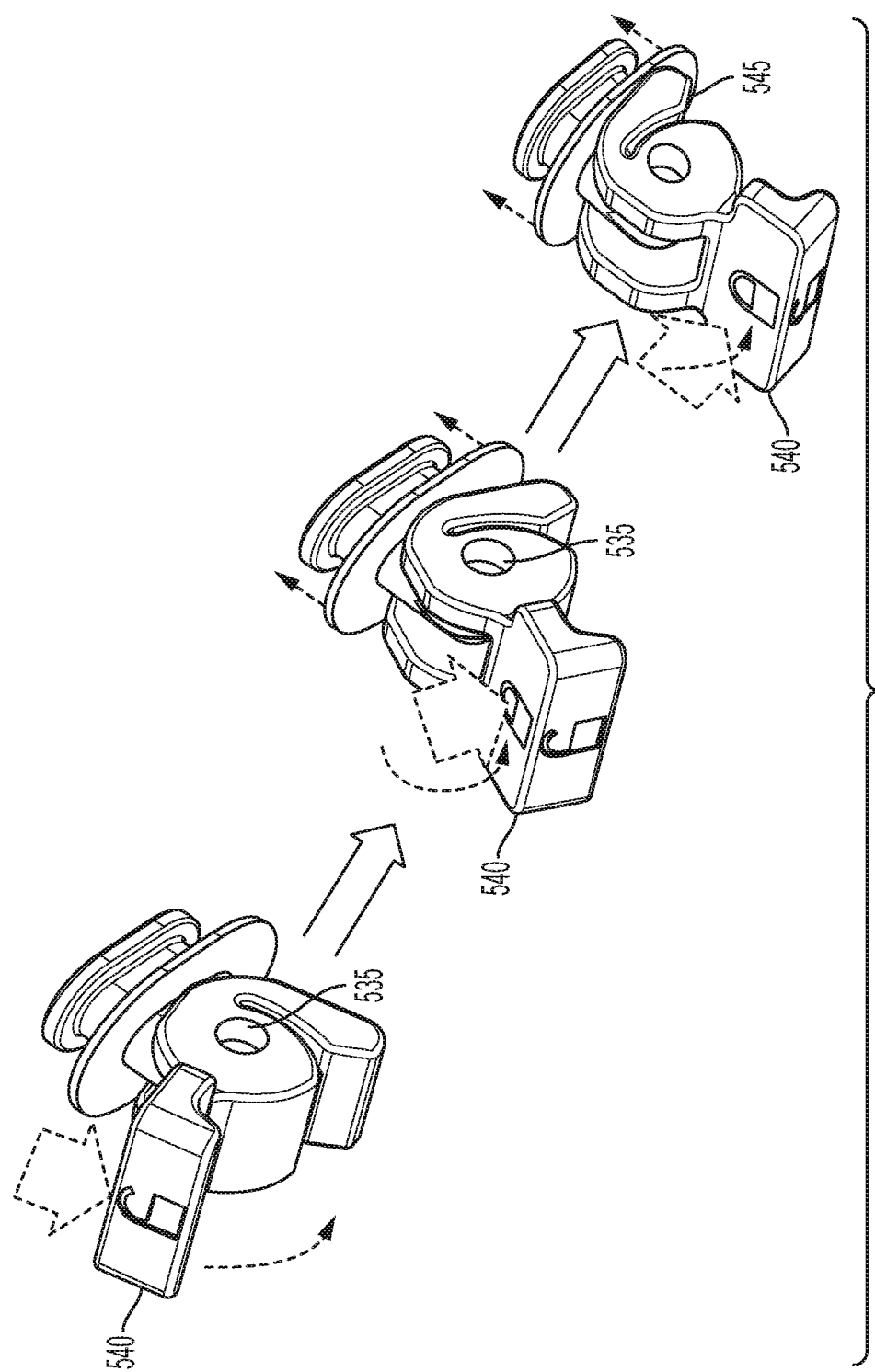

FIG. 5D depicts the interaction of the components of pitch adjustment mechanism 200 to lock and unlock the pitch adjustment of mechanism 200. In FIG. 5D, the leftmost view depicts pitch adjustment mechanism 200 in an initial, unlocked state in which the pitch of shell frame 130 (not shown) may be adjusted by moving fastener body 510 within pitch movement slot 300 of support base 120 (also not shown in FIG. 5D). As force is applied to adjustment knob 540 (shown with an arrow in the leftmost view of FIG. 5D), adjustment/locking knob 505 rotates about the adjustment pin (not shown) inserted through pin retention hole 535.

As further shown in the center view of FIG. 5D, as adjustment/locking knob 505 continues to rotate about the adjustment pin, the lower surface of knob 505, including locking extension 545, begins forcing locking spacer 500 in an upwards direction towards flange 515 of adjustment fastener 230 and also begins pulling adjustment fastener 230 in a downwards direction. As locking spacer 500 moves in the upwards direction, it applies force against the bottom surface of pitch ramp 160 of support base 120, and as adjustment fastener 230 moves in the downwards direction, the flange 515 of adjustment fastener 230 is tightened against an upper surface of shell frame 130. In another embodiment (not shown), adjustment/locking knob 505 may, instead of the reversed "e" shape shown in FIG. 5C, include a cam.

The rightmost view of FIG. 5D depicts adjustment/locking knob 505 in a locked position in which the force applied by locking spacer 500 against the bottom surface of pitch ramp 160 of support base 120, and the force applied by flange 515 of adjustment fastener 230 against an upper surface of shell frame 130 causes shell frame 130 to be held in place, at a desired pitch position, relative to support base 120. This view of FIG. 5D shows locking extension 545 in a locked position that applies the maximum upwards force against locking spacer 500 which, in turn, applies the maximum upwards force against the lower surface of support base 120. With locking extension 545 in the locked position, fastener body 510 is pulled downwards with a maximum "position locking" force, causing flange 515 to apply a maximum "position locking" force against an upper surface of shell frame 130. The "position locking" force caused by rotation of adjustment/locking knob 505 against locking spacer 500 locks shell frame 130 into a particular level of pitch. The pitch of shell frame 130 can be "unlocked" by reversing (i.e., starting with the rightmost view, and proceeding to the middle view, and then to the leftmost view) the rotation of adjustment/locking knob 505 shown in FIG. 5D. FIG. 5E shows pitch adjustment mechanism 200 rotated into a locked position, causing shell frame 130 to be held at a certain position upon pitch ramp 160 such that shell frame 130 has a certain pitch relative to support base 120.

Figure 6A:
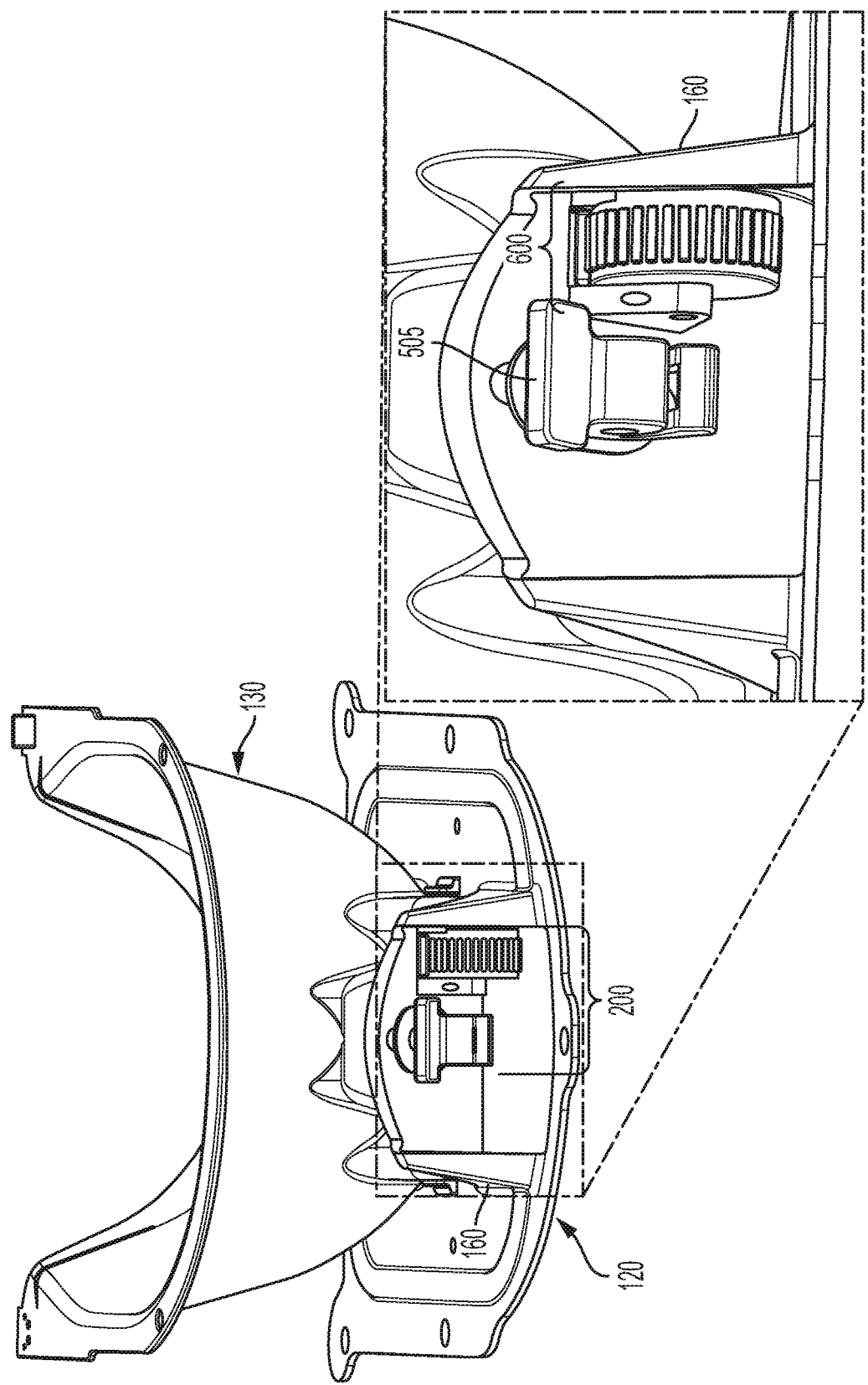
FIGS. 6A-6E depict details of an additional exemplary embodiment in which the pitch adjustment mechanism further includes a pitch adjustment wheel that permits a precise, calibrated adjustment of the pitch of shell frame relative to the support base.

FIGS. 6A-6E depict details of an additional exemplary embodiment in which pitch adjustment mechanism 200 further includes a pitch adjustment wheel assembly that permits a precise, calibrated adjustment of the pitch of shell frame 130 relative to support base 120. Pitch adjustment mechanism 200 is shown in FIG. 6A as including the additional pitch adjustment wheel assembly 600 mounted on the underside of pitch ramp 160 of support base 160, adjacent to pitch adjustment/locking knob 505.

Figure 6B:
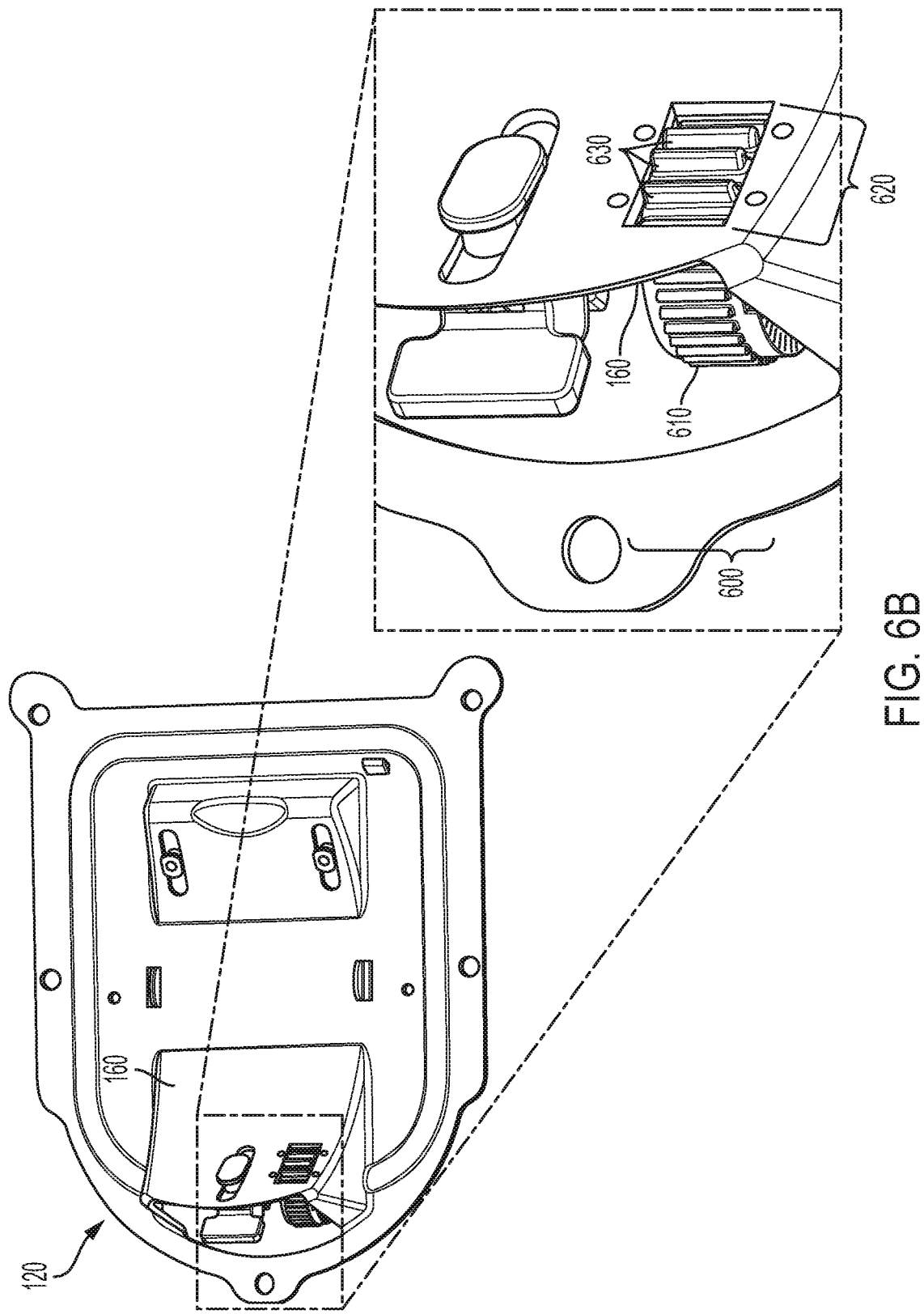

FIG. 6B further shows a top view of support base 120 and additional details of pitch adjustment wheel assembly 600. In the close-up view, pitch adjustment wheel assembly 600 is depicted as including a cylindrical pitch wheel 610 having pitch adjustment teeth 630 that extend through a rectangular pitch adjustment port 620 formed through the underside of pitch ramp 160. As can be seen in subsequent figures, the teeth of pitch wheel 610 engage with corresponding notches/slots in the underside of shell frame 130, and when pitch wheel 610 is rotated, cause the pitch of shell frame 130 to be adjusted.

Figure 6C:
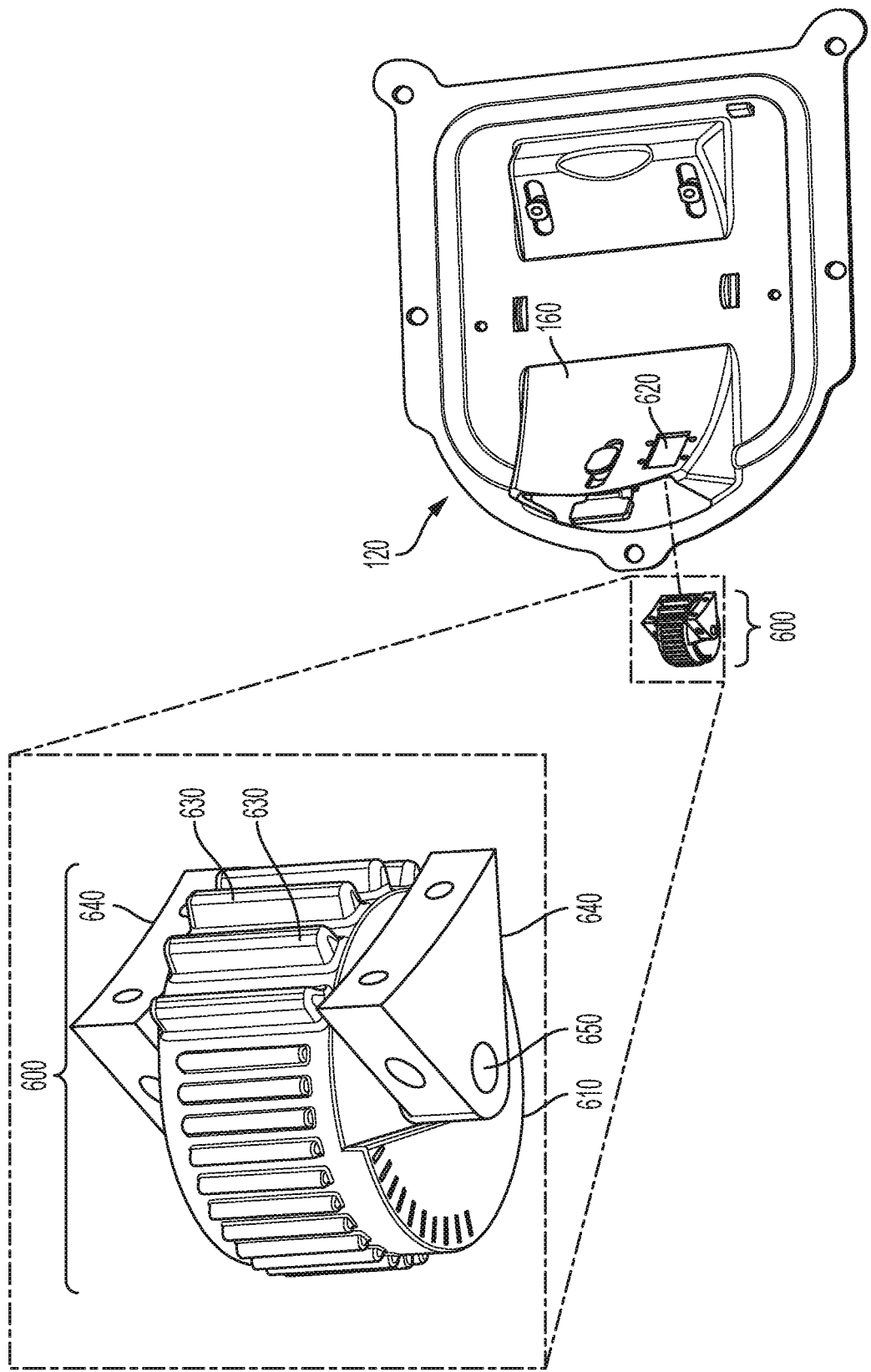

FIG. 6C depicts further details of pitch adjustment wheel assembly 600. As shown, pitch wheel 610 mounts to triangular wheel mounts 640 via a wheel axle (not shown) that extends through the wheel mount holes 650 in each of wheel mounts 640. Pitch wheel 610 may, therefore, rotate in a clockwise, or counterclockwise, direction by rotating about the wheel axle and wheel mount holes 650. As pitch wheel 610 rotates, the teeth of pitch wheel 610 that extend through pitch adjustment port 620 in pitch ramp 160, engage, as described further below with respect to FIG. 6D, the underside of shell frame 130 causing the pitch of shell frame 130 to be adjusted in periodic, discrete increments.

Figure 6D:
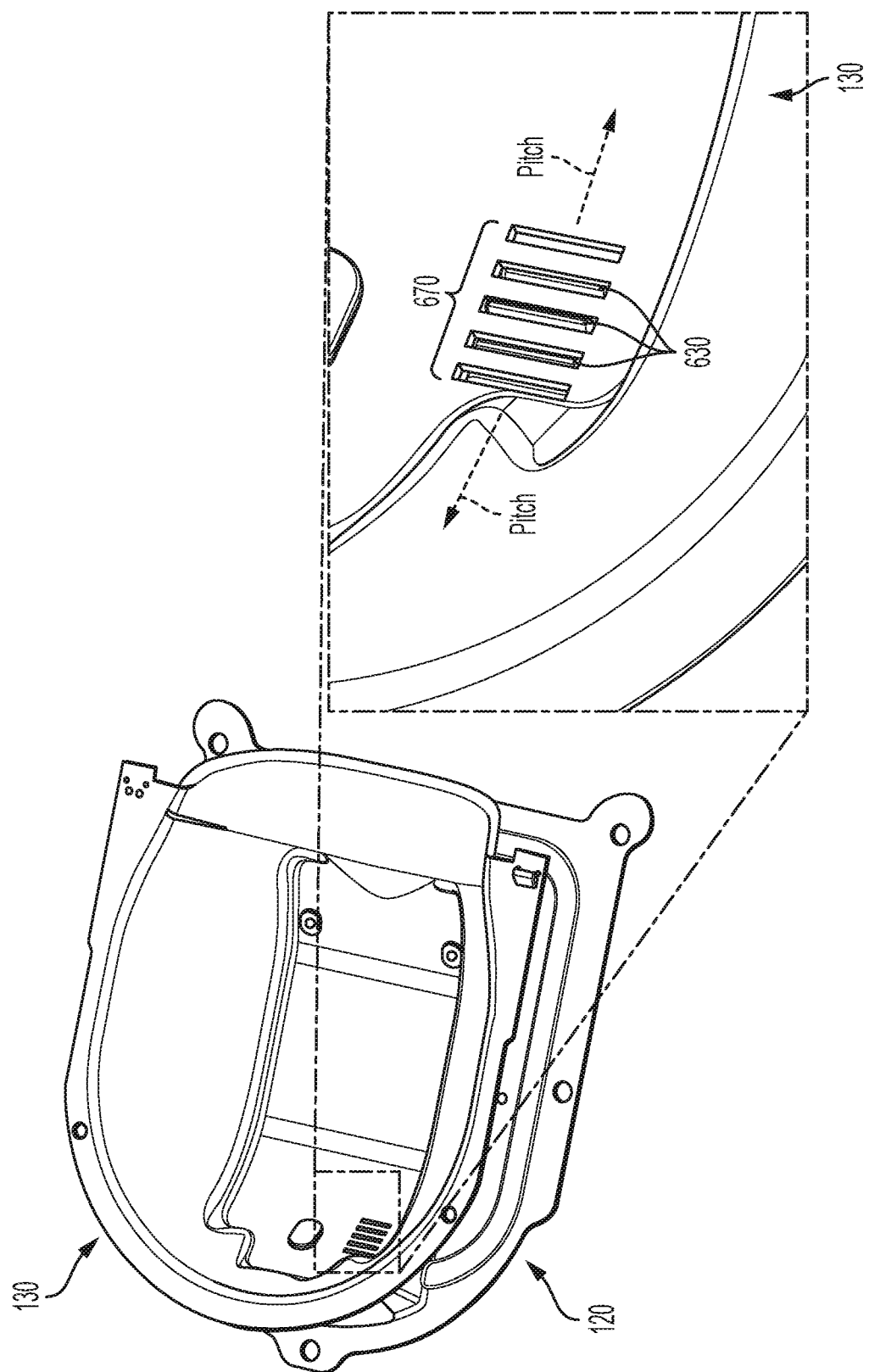

FIG. 6D depicts further details of the teeth of pitch wheel 610 adjusting the pitch of shell frame 130. As seen in FIG. 6D, shell frame 130 includes a series of pitch adjustment slots 670 that are formed from the underside of shell frame 130 through to the upper surface of shell frame 130. The pitch adjustment slots 670 match the shape and size of the teeth 630 of pitch wheel 610 located beneath shell frame 130 on the underside of support base 120. As pitch wheel 610 is rotated in a clockwise direction, the teeth 630 of pitch wheel 610 engage pitch adjustment slots 670 and cause shell frame 130 to move downwards (to the right), in the close up view of FIG. 6D. Further, as pitch wheel 610 is rotated in a counter clockwise direction, the teeth 630 of pitch wheel 610 engage pitch adjustment slots 670 and cause shell frame 130 to move upwards (to the left), in the close-up view of FIG. 6D. Each "click by click" adjustment of pitch wheel 610 causes a precise adjustment (e.g., 1°, 0.5°, etc.) of the pitch of shell frame 130 via interaction of the teeth 630 of pitch wheel 610 with the pitch adjustment slots 670 of shell frame 130.

Figure 6E:
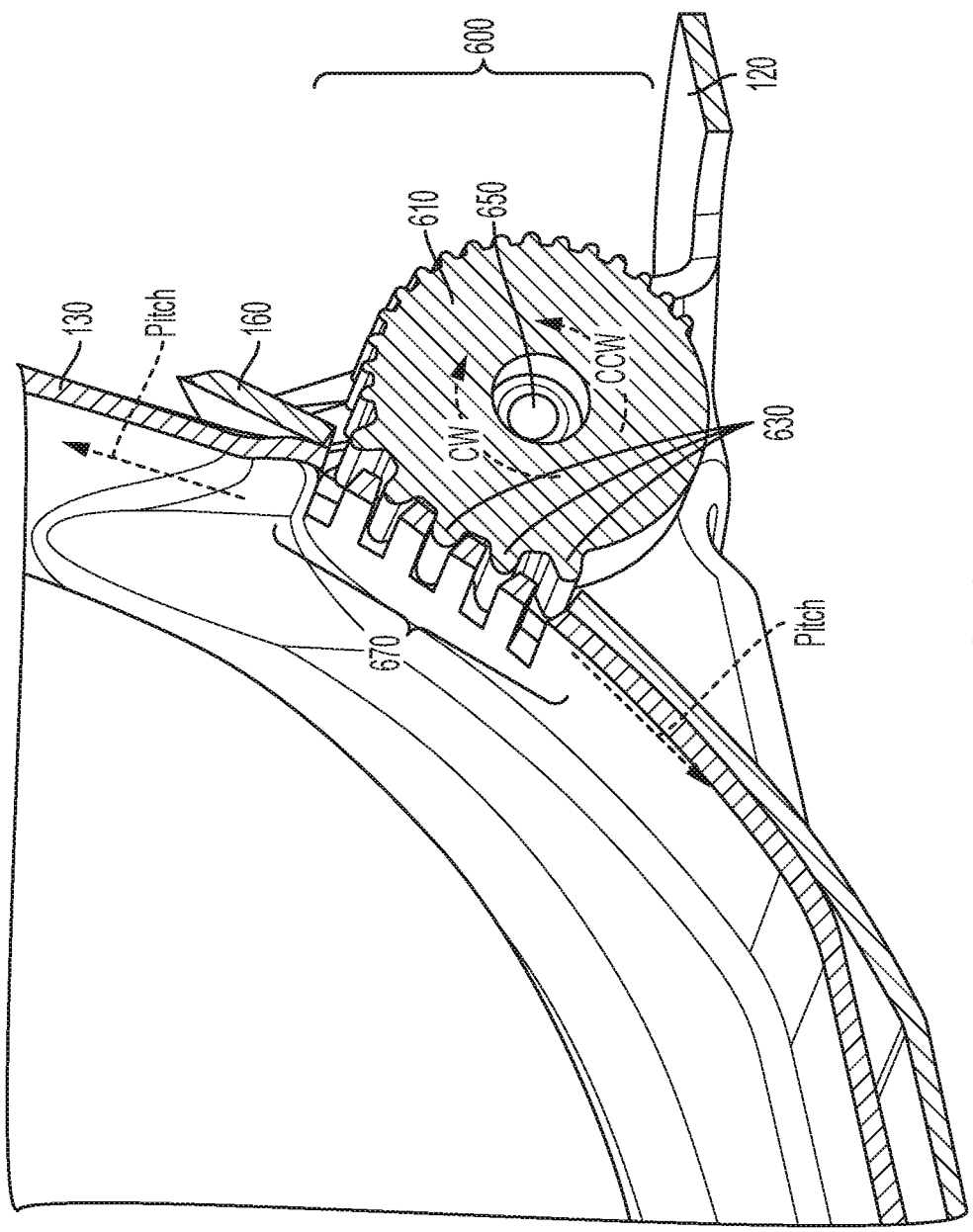

FIG. 6E depicts a cross-sectional cutaway view of pitch adjustment wheel assembly 600. As pitch wheel 610 is rotated in a clockwise direction ("CW"), the teeth 630, extending through pitch adjustment port 620 in pitch ramp 160, engage with the pitch adjustment slots 670 in the bottom surface of shell frame 130. Engagement of the teeth 630 of pitch wheel 610 with pitch adjustment slots 670 causes shell frame 130 to move upwards, in the view shown in FIG. 6E, as pitch wheel 610 is rotated clockwise. Alternatively, as pitch wheel 610 is rotated in a counter-clockwise (CCW) direction, the teeth 630, extending through pitch adjustment port 620 in pitch ramp 160, engage with the pitch adjustment slots 670 in the bottom surface of shell frame 130. Engagement of the teeth 630 of pitch wheel 610 with pitch adjustment slots 670 causes shell frame 130 to move downwards, in the view shown in FIG. 6E, as pitch wheel 610 is rotated counter clockwise.

Figure 7:
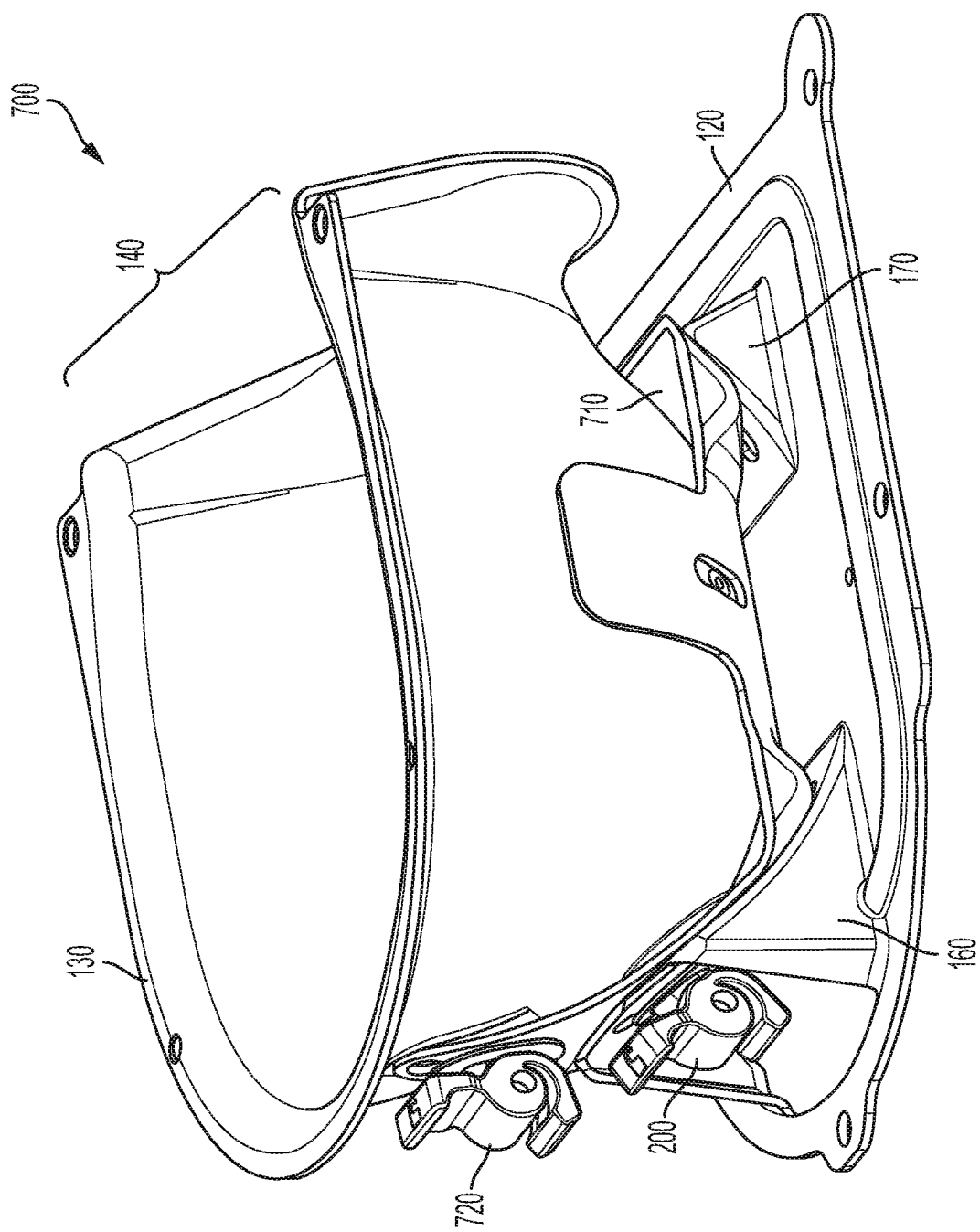
FIG. 7 illustrates another exemplary embodiment of a body part immobilization device that includes, in addition to a pitch adjustment mechanism, a roll adjustment mechanism.

FIG. 7 illustrates another exemplary embodiment of a body part immobilization device 700 that includes, in addition to a pitch adjustment mechanism, a roll adjustment mechanism that permits the shell frame 130 (and the patient body part placed within the shell frame 130), to be "rolled" relative to the support base 120 of the device 700. As shown in FIG. 7, body part immobilization device 700 includes a support base 120 and a shell frame 130 similar to the embodiment of FIG. 1. Shell frame 130 may include an approximate half shell structure having an inner surface that is configured to conform to a back of the patient's body part (e.g., head and neck). In the implementation depicted in FIG. 7, the half shell structure of shell frame 130 has a shape that approximates half of a three-dimensional spheroid, where the half roughly transects a vertical center of the spheroid. Shell frame 130 may include a cutout 140 in one side of the shell frame 130 that is configured to conform to the body part (e.g., neck or other body part) of the patient and enables, when the patient's body part (e.g., head) is laid within shell frame 130, the attaching body component (e.g., neck) to extend out of the interior of shell frame 130. Support base 120 may be configured similarly to that shown, and described, above with respect to body part immobilization device 100.

As shown in FIG. 7, device 700 further includes a shell frame carriage 710 upon which shell frame 130 rests. Shell frame carriage 710 rests upon first pitch ramp 160 and second pitch ramp 170, which are further disposed on support base 120 opposite one another and at a sufficient distance apart to enable the lower surface of shell frame carriage 710 to rest upon support base 120 between the two pitch ramps 160 and 170 when oriented in a horizontal, non-pitch adjusted position. Pitch ramp 160 and pitch ramp 170 include sloping ramps that extend downwards towards a center of support base 120. Shell frame 130, shell frame carriage 710, and support base 120 may be formed from various types of materials, including, for example, metal, plastic, carbon fiber, and/or a composite material. Shell frame 130, shell frame carriage 710, and support base 120 may each be formed from a same type of material, or a different type of material. For example, support base 120 may be formed from metal, and shell frame 130 and shell frame carriage 710 may be formed from a plastic or a composite material. As shown in FIG. 7, and described in further detail below, device 700 includes a pitch adjustment mechanism 200 for adjusting the pitch of shell frame 130 and shell frame carriage 710, and additionally includes a roll adjustment mechanism 720 for adjusting the roll of shell frame 130.

FIG. 8A depicts an exploded three-dimensional view of body part immobilization device 700 of FIG. 7. Support base 120 includes a similar physical configuration to that described with respect to device 100 of FIGS. 1A-1F above. Shell frame carriage 710 includes a tray-like shape having an upper surface that conforms to the spheroid lower surface of shell frame 130, and a lower surface that conforms to the upper surface of support base 120, including the upper surface of pitch ramp 160 and pitch ramp 170. As shown, the lower surface of shell frame carriage 710 rests upon the upper surface of support base 120, including resting on the upper surfaces of pitch ramp 160 and pitch ramp 170. The lower surface of shell frame 130 rests upon the upper surface of shell frame carriage 710, with shell movement pins 800 extending through holes in shell frame 130 into corresponding shell movement slots (described in further detail below) in shell frame carriage 710. Pitch adjustment mechanism 200 enables the adjustment of the pitch of shell frame carriage 710, which further adjusts the pitch of shell frame 130 that rides within shell frame carriage 710. Roll adjustment mechanism 720 enables the adjustment of the roll of shell frame 130 within shell frame carriage 710.

Figure 8B:
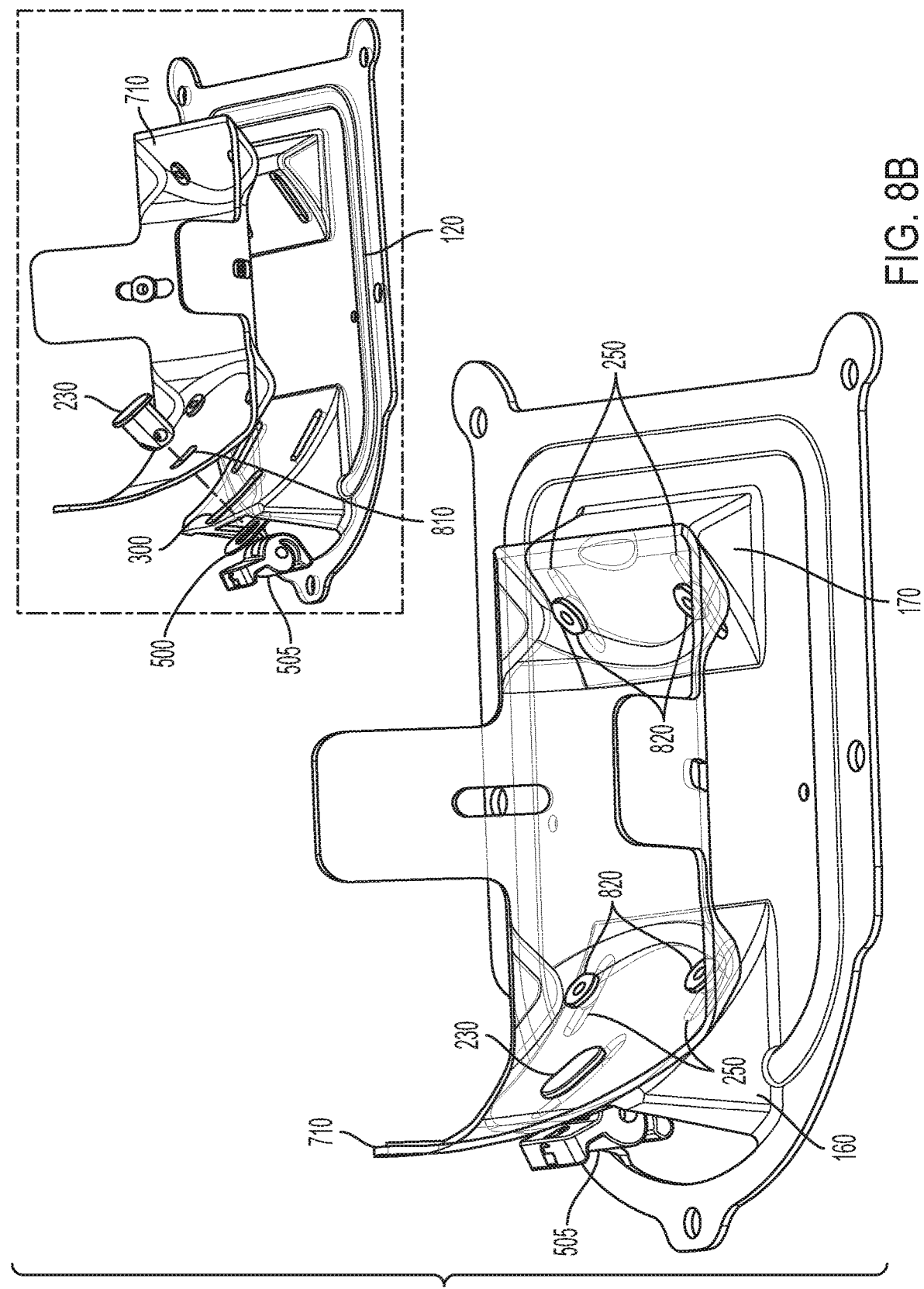
FIG. 8B is a three-dimensional view of the components of the body part immobilization device of FIG. 7 that are involved in adjustment of the pitch of the shell frame carriage and the shell frame.

FIG. 8B is a three-dimensional view of the components of body part immobilization device 700 that are involved in adjustment of the pitch of shell frame carriage 710 and shell frame 130. As shown in the main view of FIG. 8B, carriage movement pins 820 extend through corresponding holes in shell frame carriage 710 into movement slots 250 within pitch ramp 160 and pitch ramp 170. As further depicted in the break-out view of FIG. 8B, adjustment fastener 230 of pitch adjustment mechanism 200 extends through a hole 810, in a rear surface of shell frame carriage 710, that is located so as to align with pitch adjustment slot 300 within pitch ramp 160. Locking spacer 500 fits over adjustment fastener 230, and adjustment/locking knob 505 fits over, and attaches to, adjustment fastener 230. Operation of adjustment/locking knob 505 may enable the pitch of shell frame carriage 710 and shell frame 130 to be "locked" into a certain pitch position. Operation of the pitch adjustment of body part immobilization device 700 is described in further detail below with respect to FIGS. 11A and 11B.

FIG. 8C is a three-dimensional view of the components of body part immobilization device 700 that are involved in adjustment of the roll of shell frame 130. As shown in the main view of FIG. 8C, shell movement pins 800 extend through corresponding holes in shell frame 130 into movement slots 830 within shell frame carriage 710, where movement slots 830 are oriented in a transverse direction to movement slots 250 in pitch ramps 160 and 170. As further depicted in the break-out view of FIG. 8C, adjustment fastener 230 of roll adjustment mechanism 720 extends through a roll fastener hole 850 within shell frame 130, and through a corresponding hole 840 in a forward surface of shell frame carriage 710 that is aligned with the roll fastener hole 850 within shell frame 130. Hole 840 in shell frame carriage 710 is sized larger than roll fastener hole 850 in shell frame 130 to permit rotational "roll" movement of shell frame 130. Locking spacer 500 fits over adjustment fastener 230, and adjustment/locking knob 505 fits over, and attaches to, adjustment fastener 230 such as described with respect to FIG. 5C above. Operation of adjustment/locking knob 505 may enable the roll of shell frame 130, within shell frame carriage 710, to be "locked" into a certain roll position.

Operation of the roll adjustment of body part immobilization device 700 is described in further detail below with respect to FIGS. 13A and 13B.

Figure 9B:
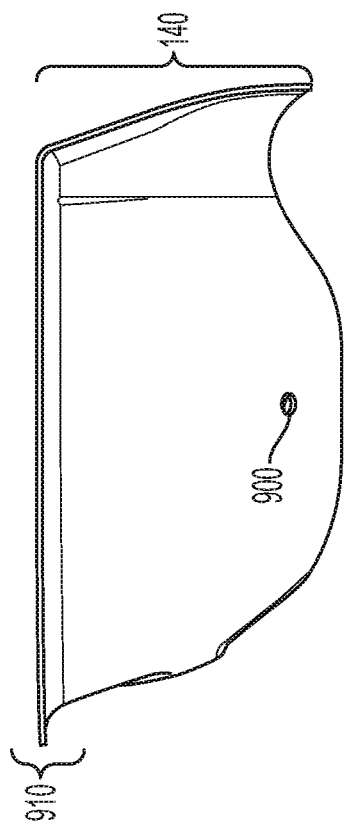
FIGS. 9A-9D depict four different views of the shell frame of the body part immobilization device of FIG. 7.
Figure 9D:
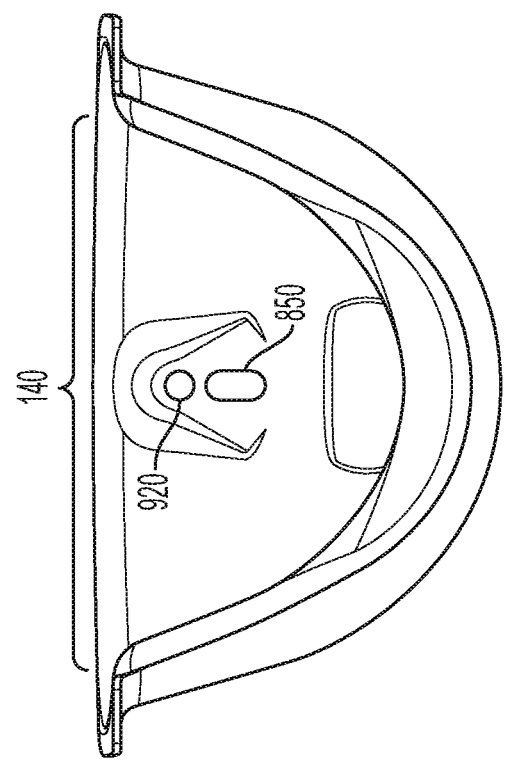
Figure 9A:
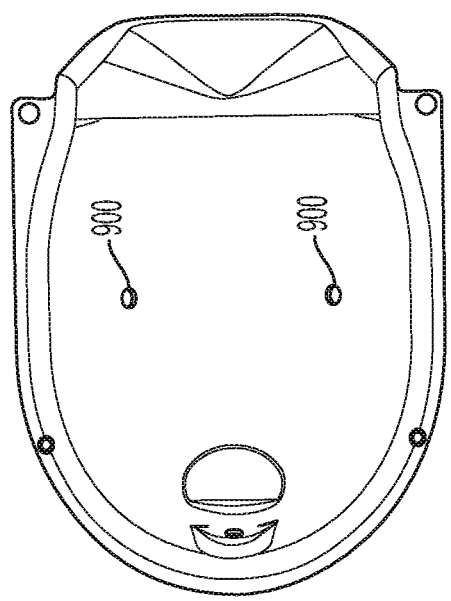
Figure 9C:
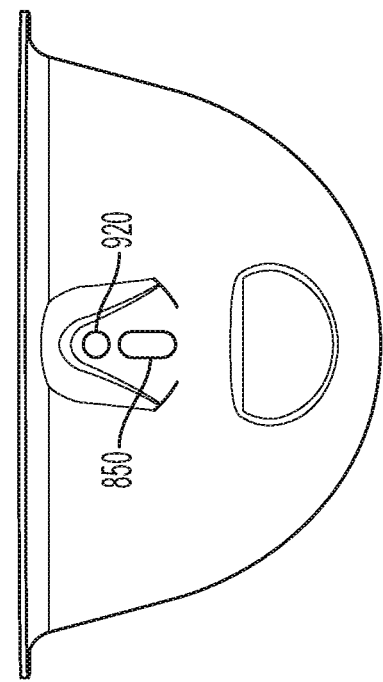

FIGS. 9A-9D depict four different views of shell frame 130 of body part immobilization device 700, including a top view in FIG. 9A, a side view in FIG. 9B, a rear view in FIG. 9C, and a front view in FIG. 9D. As can be seen in the views of FIGS. 9A-9D, shell frame 130 includes a half shell structure having an inner surface that is configured to conform to a back of the patient's head and neck. The half shell structure of shell frame 130 has a shape that approximates half of a three-dimensional spheroid, where the half roughly transects a center of the spheroid. Shell frame 130 may include a neck cutout 140 in one side of the shell frame 130 that includes an opening in the half shell that is configured to conform to the neck 150 (not shown) of the patient and enables, when the patient's head 110 (not shown) is laid within shell frame 130, the neck 150 (not shown) to extend out of the interior of shell frame 130 through the neck cutout 140.

As shown in FIGS. 9A-9D, an upper edge of shell frame 130 includes a flange 910 that extends around a perimeter of the upper edge of the shell frame 130. The flange 910 extends approximately ½ to ¾ of an inch out from the upper edge of shell frame 130. As can further be seen in FIGS. 9A and 9B, shell frame 130 includes two shell movement pin holes 900 located in the vicinity of the bottom of shell frame 130. Shell movement pin holes 900 receive corresponding shell movement pins 800 (not shown) and line up with respective movement slots 830 (not shown) within shell frame carriage 710 (not shown). FIGS. 9C and 9D further depict roll fastener hole 850 and rotation hole 920. Though not shown in FIGS. 9C and 9D, adjustment fastener 230 of roll adjustment mechanism 720 extends through roll fastener hole 850 into hole 840 in shell frame carriage 710, and a fastening mechanism, such as, for example, a screw and nut, extends through rotation hole 920 to rotatably fasten shell frame 130 to shell frame carriage 710 such that shell frame 130 may rotate about a central axis formed within rotation hole 920 as the roll of shell frame 130 is adjusted relative to shell frame carriage 710 and support base 120. Flange 910 of device 700 may be similar to flange 400 of device 100, with multiple registration and alignment holes being disposed around a perimeter of flange 910, and with each registration hole extending from an upper surface of flange 910 through to a lower surface of flange 910. The frame of the body part mask (not shown) may include multiple pins, on an underside of the frame, that line up with, and can be inserted into, the registration and alignment holes of flange 910. Therefore, when docking the body part mask to shell frame 130, the registration and alignment holes of flange 910, in conjunction with the multiple pins on the underside of the body part mask frame, ensure the proper positioning of the body part mask relative to shell frame 130.

Figure 10A:
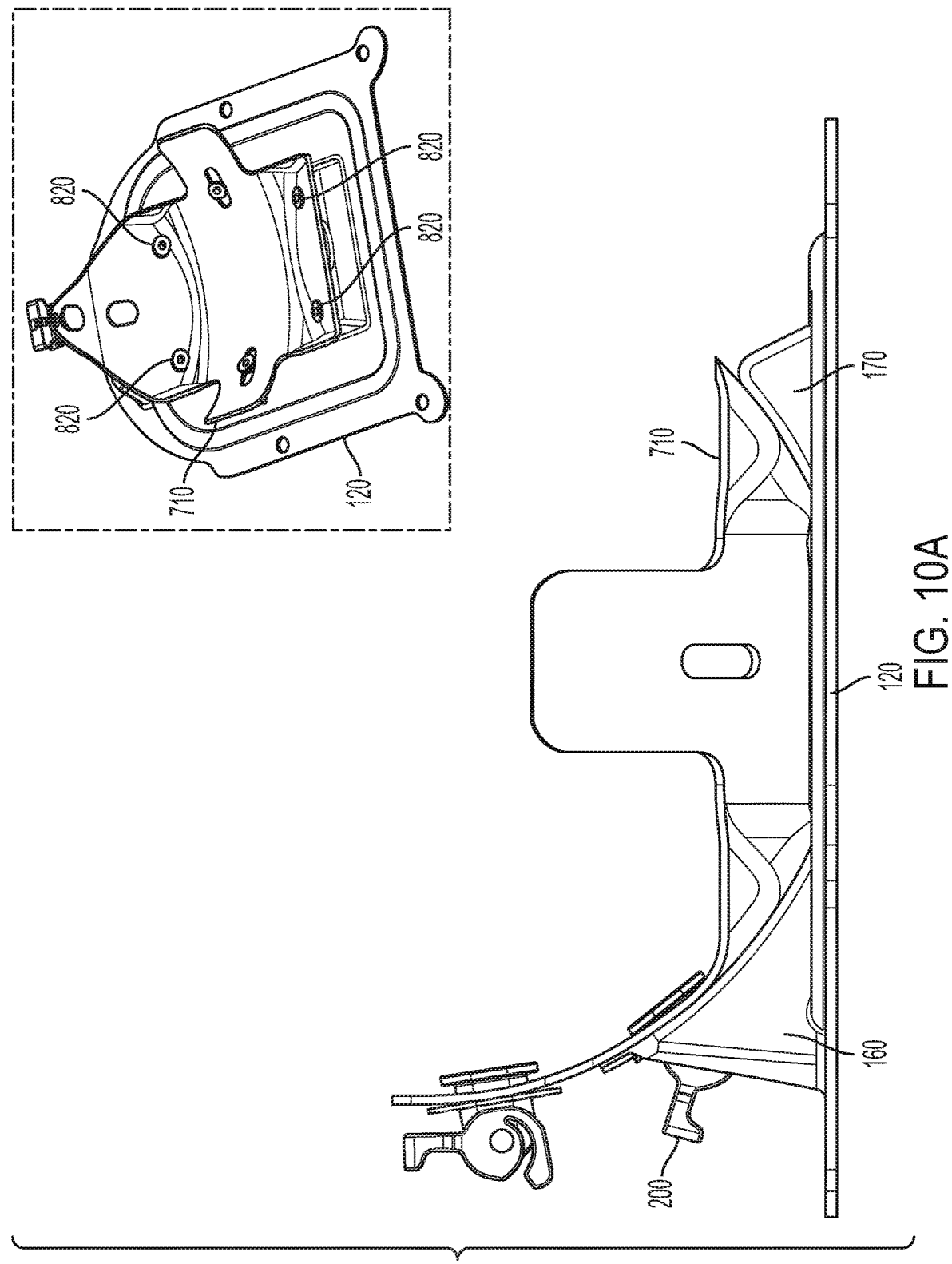
FIGS. 10A and 10B depict the support base and the shell frame carriage of the device of FIG. 7 in a horizontal position prior to any adjustment being applied to change the pitch of the shell frame carriage relative to the support base.
Figure 10B:
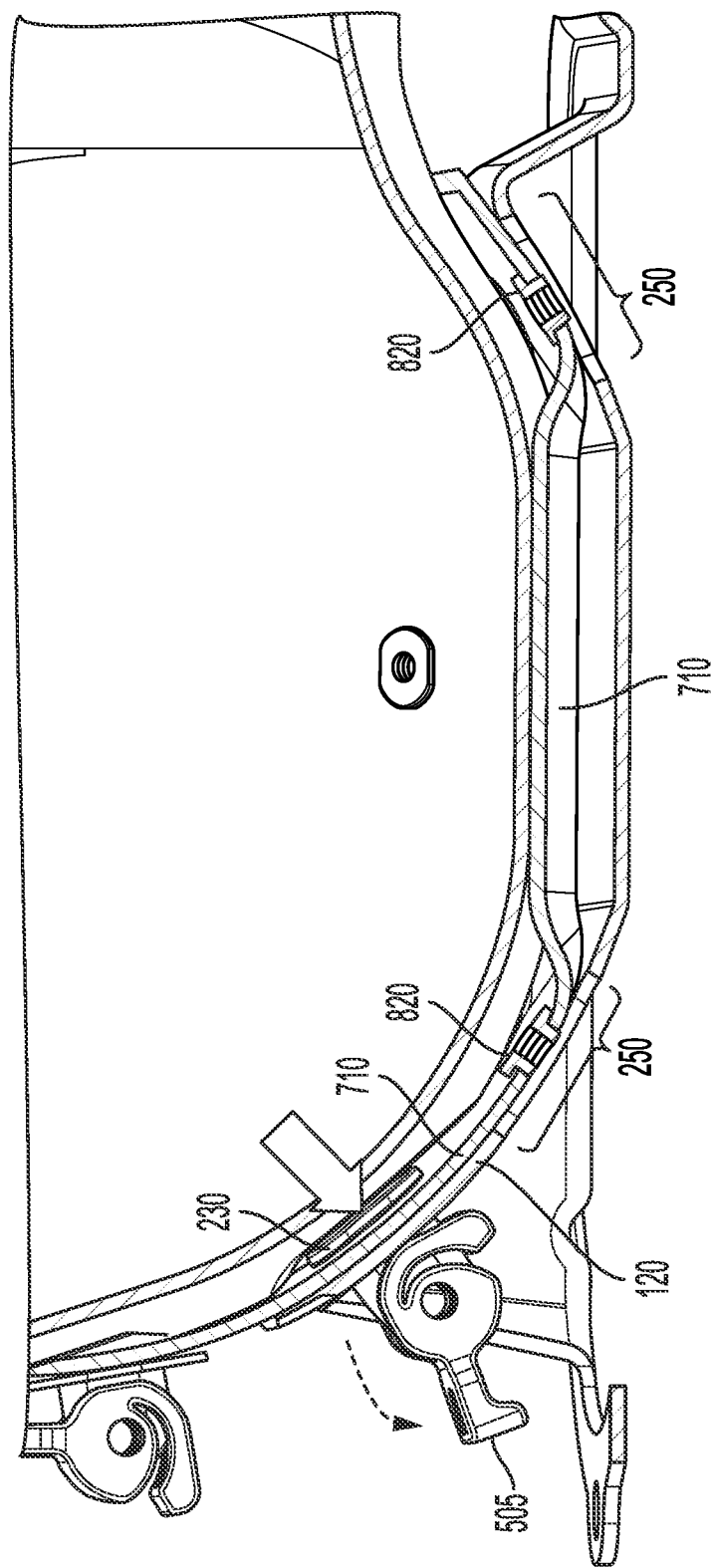

FIGS. 10A and 10B depict support base 120 and shell frame carriage 710 of device 700 in a horizontal position prior to any adjustment being applied to change the pitch of shell frame carriage 710 relative to support base 120. With shell frame carriage 710 residing in a non-pitch adjusted position, such as shown in FIGS. 10A and 10B, shell frame carriage pins 820 extend through corresponding holes in shell frame carriage 710 and into carriage movement slots 250 (not shown) of pitch ramps 160 and 170 at a midpoint within the length of slots 250. To adjust the pitch of shell frame carriage 710 and shell frame 130, adjustment/locking knob 505 of pitch adjustment mechanism 200 may be rotated to an "unlocked" position. As can be seen in FIG.

10B, when adjustment/locking knob 505 is rotated to a locked position, adjustment fastener 230 pulls shell frame carriage 710 against the upper surface of support base 120 such that shell frame carriage 710 (and shell frame 130, which rests within carriage 710) is held in a fixed pitch position relative to support base 120. To adjust the pitch of shell frame carriage 710 and shell frame 130, adjustment/locking knob 505 of pitch adjustment mechanism 200 may be rotated to an unlocked position (the opposite direction to that shown in FIG. 10B), loosening the hold adjustment fastener 230 has on shell frame carriage 710. With adjustment/locking knob 505 rotated to an unlocked position, adjustment fastener 230 no longer pulls shell frame carriage 710 against the upper surface of support base 120, thus, enabling the pitch of shell frame carriage 710 and shell frame 130 to be adjusted, as described below with respect to FIGS. 11A and 11B. When the pitch of shell frame carriage 710 is adjusted, carriage movement pins 820 ride within movement slots 250 of support base 120, either to the left or to the right, in the view depicted in FIG. 10B, depending on the direction of pitch being applied to shell frame carriage 710 and shell frame 130.

FIGS. 11A and 11B depict adjustment of the pitch of shell frame carriage 710 (and shell frame 130, which rides within carriage 710). In FIG. 11A, the rear of shell frame carriage 710, and shell frame 130 (not shown) resting within carriage 710, is pitched upwards upon pitch ramp 160 and the front of shell frame carriage 710 is simultaneously pitched downwards upon pitch ramp 170 by sliding the lower surface of carriage 710 upon pitch ramps 160 and 170. As the pitch of shell frame carriage 710 is adjusted, carriage movement pins 820 ride within movement slots 250 (not shown) of support base 120. Each of movement slots 250 has a slot length that limits that amount of pitch adjustment in either direction. In FIG. 11B, the rear of shell frame carriage 710, and the shell frame 130 (not shown) resting within carriage 710, is pitched downwards upon pitch ramp 160 and the front of shell frame carriage 710 is simultaneously pitched upwards upon pitch ramp 170 by sliding the lower surface of carriage 710 upon pitch ramps 160 and 170.

Figure 12:
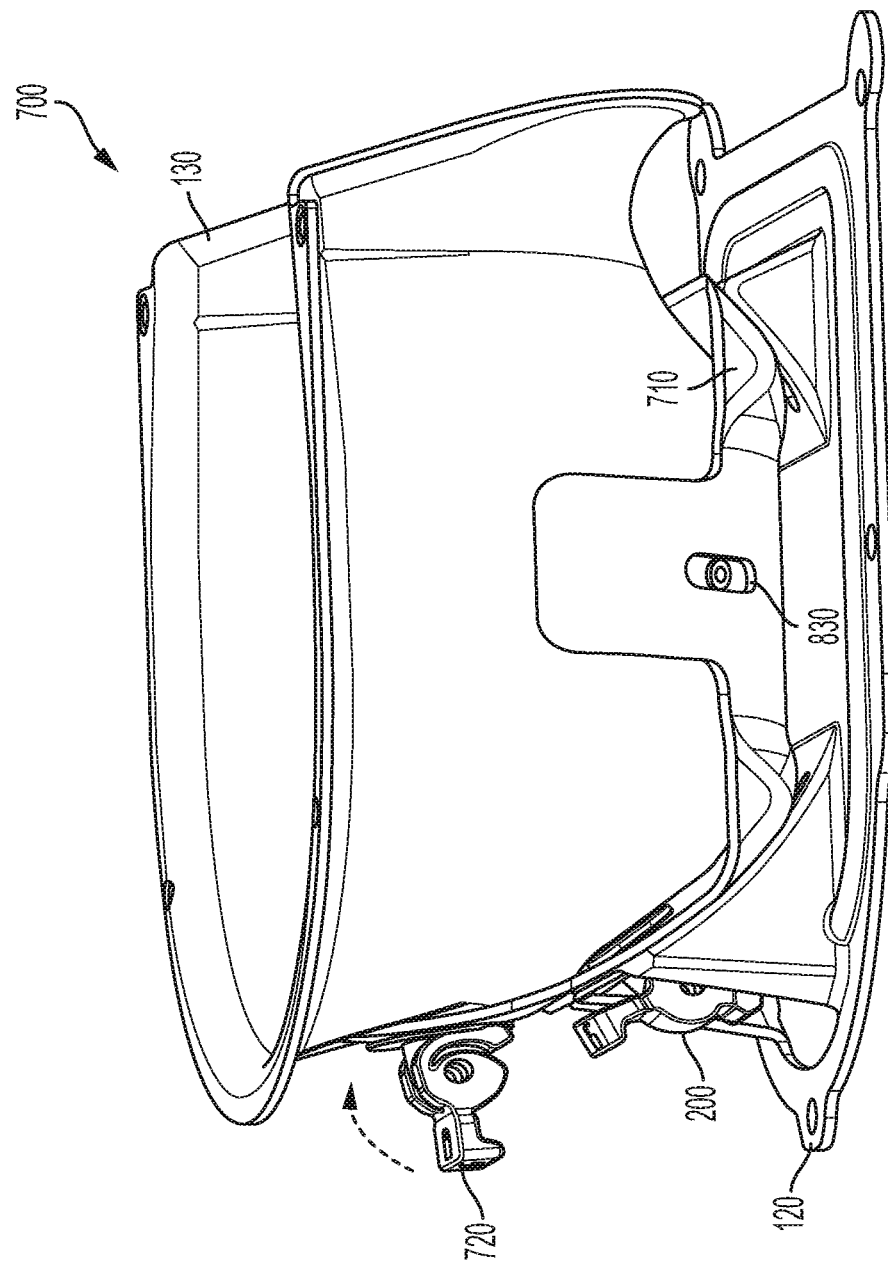
FIG. 12 depicts the shell frame, the shell frame carriage, and the support base of the device of FIG. 7 in a horizontal position prior to any roll adjustment being applied to change the roll of the shell frame relative to the shell frame carriage and the support base.

FIG. 12 depicts shell frame 130, shell frame carriage 710, and support base 120 of device 700 in a horizontal position prior to any roll adjustment being applied to change the roll of shell frame 130 relative to shell frame carriage 710 and support base 120. With shell frame 130 residing in a non-roll adjusted position, such as shown in FIG. 12, shell frame pins 800 (not shown) extend into corresponding shell movement slots 830 in shell frame carriage 710 at a midpoint within the length of slots 830. To adjust the roll of shell frame 130, adjustment/locking knob 505 of roll adjustment mechanism 720 may be rotated from a "locked" position to an "unlocked" position (shown with the arrow in an upward direction in FIG. 12). In the exemplary implementation depicted in FIG. 12, when adjustment/locking knob 505 is rotated to an unlocked position, adjustment fastener 230 no longer pulls shell frame 130 against the upper surface of shell frame carriage 710 such that shell frame 130 is not held in a fixed position relative to shell frame carriage 710, and the roll of shell frame 130 may be adjusted using roll adjustment mechanism 720.

The operation of roll adjustment mechanism 710 is described in further detail with reference to FIG. 5D. In the rightmost view of FIG. 5D, adjustment/locking knob 505 is in a locked position in which the force applied by locking spacer 500 against the bottom surface of shell frame carriage 710, and the force applied by flange 515 of adjustment fastener 230 against an upper surface of shell frame 130 causes shell frame 130 to be held in place, at a desired roll position, relative to shell frame carriage 710 and support base 120. This rightmost view of FIG. 5D shows locking extension 545 in a locked position that applies the maximum upwards force against locking spacer 500 which, in turn, applies the maximum upwards force against the lower surface of shell frame carriage 710. With locking extension 545 in the locked position, fastener body 510 is pulled downwards with a maximum "position locking" force, causing flange 515 to apply a maximum "position locking" force against an upper surface of shell frame 130. The "position locking" force caused by rotation of adjustment/locking knob 505 against locking spacer 500 locks shell frame 130 into a particular level of roll relative to shell frame carriage 710. The roll of shell frame 130 can be "unlocked" by reversing (i.e., starting with the rightmost view, and proceeding to the middle view, and then to the leftmost view) the rotation of adjustment/locking knob 505 shown in FIG. 5D.

Figure 13A:
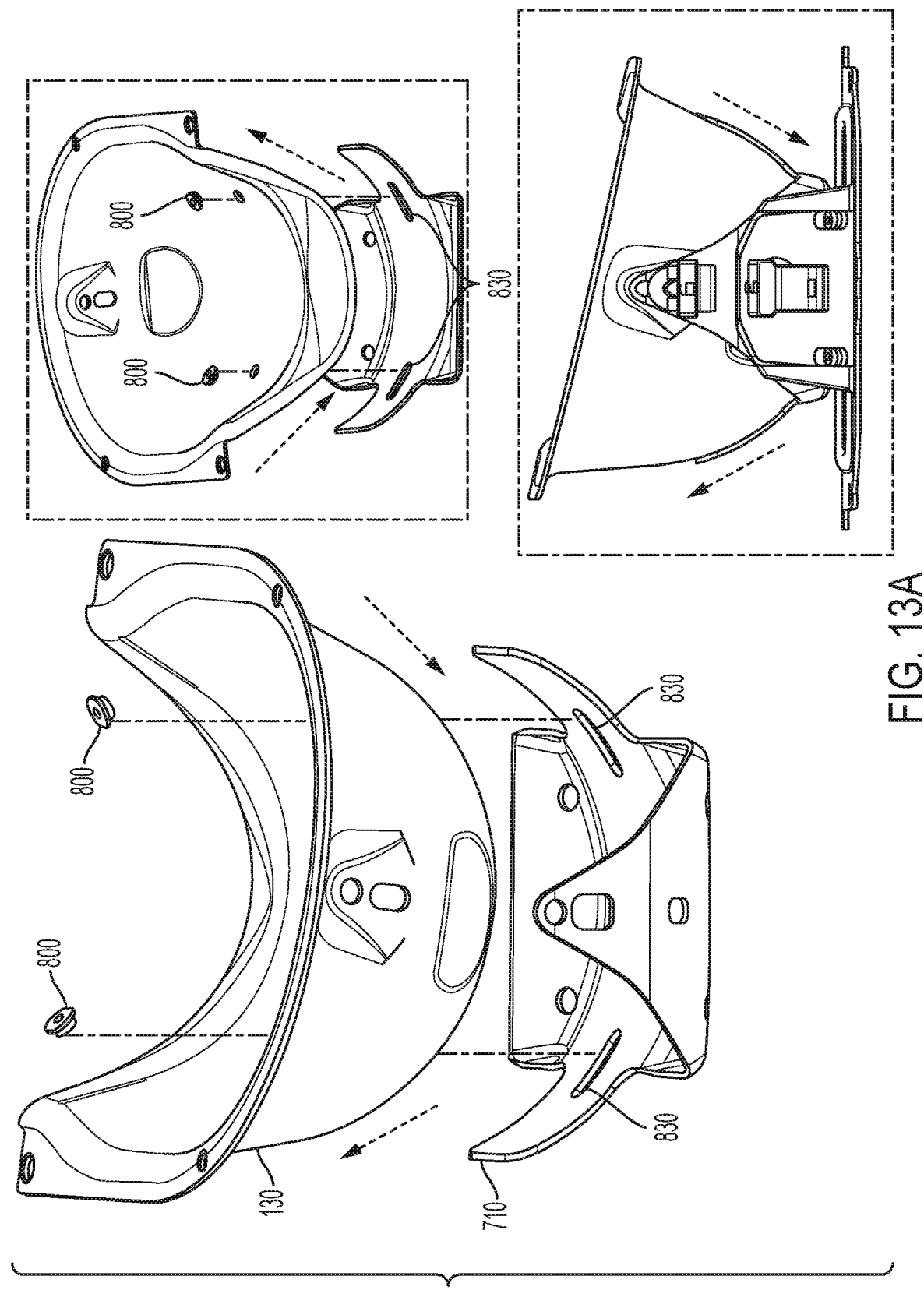

FIGS. 13A and 13B depict adjustment of the roll of shell frame 130 relative to shell frame carriage 710 and support base 120. In FIG. 13A, the right side of shell frame 130 (viewed from the rear of shell frame 130) is rolled downwards upon shell frame carriage 710, and the left side of shell frame 130 is simultaneously rolled upwards upon shell frame carriage 710 by sliding the lower surface of shell frame 130 along the upper surface of shell frame carriage 710. As the roll of shell frame 130 is adjusted, shell movement pins 800 ride within shell movement slots 830 of shell frame carriage 710. Each of shell movement slots 830 has a slot length that limits that amount of roll adjustment in either direction. In FIG. 13B, the right side of shell frame 130 (viewed from the rear of shell frame 130) is rolled upwards upon shell frame carriage 710 and the left side of shell frame 130 is simultaneously rolled downwards upon shell frame carriage 710, by sliding the lower surface of shell frame 130 along the upper surface of shell frame carriage 710, to roll adjust shell frame 130 in an opposite direction to that depicted in FIG. 13A. Once the roll of shell frame 130 has been adjusted to the desired roll position, adjustment/locking knob 505 of roll adjustment mechanism 720 may be rotated to a locked position to tighten adjustment fastener 230 against shell frame 130. With adjustment/locking knob 505 rotated to a locked position, adjustment fastener 230 pulls shell frame 130 against the upper surface of shell frame carriage 710, thus, holding shell frame 130 in a fixed roll position relative to shell frame carriage 710 and support base 120.

FIGS. 7-13B depict an exemplary embodiment of body part immobilization device 700 that includes both a pitch adjustment mechanism and a roll adjustment mechanism. In other embodiments, however, body part immobilization device 700 may include only the roll adjustment mechanism 720 (and associated structure), and may not include the pitch adjustment mechanism (i.e., pitch adjustment mechanism 200, and associated structure, is omitted from device 700).

The foregoing description of implementations provides illustration and description, but is not intended to be exhaustive or to limit the invention to the precise form disclosed. Modifications and variations are possible in light of the above teachings or may be acquired from practice of the invention. Although the invention has been described in detail above, it is expressly understood that it will be apparent to persons skilled in the relevant art that the invention may be modified without departing from the spirit of the invention. Various changes of form, design, or arrangement may be made to the invention without departing from the spirit and scope of the invention. Therefore, the above-mentioned description is to be considered exemplary, rather than limiting, and the true scope of the invention is that defined in the following claims. For example, support base 120 is shown and described above as having a certain structure that allows shell frame 130 or shell frame carriage 710 to ride upon support base 120. In other implementations, however, support base 120 may include a different type of supporting structure, such as a base plate or a couch top, having a physical configuration that also enables shell frame 130 or shell frame carriage 710 to ride upon the support base. In such implementations, the different types of supporting structure may include a matching hole pattern for adjustment pins similar to that shown in FIGS. 3A-3D or FIG. 8A.

No element, act, or instruction used in the description of the present application should be construed as critical or essential to the invention unless explicitly described as such. Also, as used herein, the article "a" is intended to include one or more items. Further, the phrase "based on" is intended to mean "based, at least in part, on" unless explicitly stated otherwise.

What is claimed is:

1. A structure for positioning a body part, comprising: a support base comprising a planar member, a first concave ramp, and an opposing, second concave ramp, wherein a first slope of the first concave ramp faces a second slope of the opposing, second concave ramp and wherein a first upper surface of the first slope of the first concave ramp slopes downwards towards the second concave ramp to connect to an upper surface of the planar member and a second upper surface of the second slope of the second concave ramp slopes downwards towards the first concave ramp to connect to the upper surface of the planar member, and wherein a portion of the upper surface of the planar member separates, and extends between, the first upper surface of the first concave ramp and the second upper surface of the second concave ramp; and a shell frame, having an inner surface configured to a shape of the body part and an outer convex surface, wherein the outer convex surface of the shell frame is further configured to: ride upon, and move relative to, an upper surface of a carriage, that further resides upon the first upper surface of the first concave ramp and the second upper surface of the second concave ramp, to enable a roll of the shell frame to be adjusted relative to the support base, wherein, when the outer convex surface of the shell frame is configured to ride upon, and move relative to, an upper surface of the carriage, the structure further comprises a roll adjustment mechanism configured to facilitate adjustment of the roll of the shell frame relative to the support base.

2. The structure of claim 1, wherein, wherein the structure further comprises:
a pitch adjustment mechanism configured to facilitate adjustment of the pitch of the shell frame relative to the support base.

3. The structure of claim 2, wherein the pitch adjustment mechanism comprises an adjustment fastener that extends through the support base and through the carriage.

4. The structure of claim 3, wherein the pitch adjustment mechanism further comprises a locking spacer and an adjustment knob and wherein the adjustment knob connects to the adjustment fastener, and wherein the adjustment knob is rotatable to cause the locking spacer to tighten against a surface of the support base to lock the shell frame into a specific pitch position.

5. The structure of claim 2, wherein the pitch adjustment mechanism further comprises a pitch adjustment wheel, having a plurality of adjustment positions, wherein the pitch adjustment wheel is rotatable to the plurality of adjustment positions to adjust the pitch of the shell frame to a calibrated pitch position.

6. The structure of claim 1, wherein the shell frame comprises an approximate half shell having a cut-out portion configured to receive the body part, wherein the approximate half shell further comprises half of a three-dimensional spheroid, and wherein an upper edge of the approximate half shell comprises a flange that extends around a portion of a perimeter of the upper edge of the half shell.

7. The structure of claim 1, wherein the roll adjustment mechanism comprises an adjustment fastener that extends through the carriage and the shell frame, a locking spacer and an adjustment knob and wherein the adjustment knob connects to the adjustment fastener, and wherein the adjustment knob is rotatable to cause the locking spacer to tighten against a surface of the carriage to lock the shell frame into a specific roll position.

8. A structure, comprising:
a support base configured to be positioned on a flat surface and to receive a shell frame, or a carriage upon which the shell frame rests, and comprising:
a planar member, a first ramp, an opposing, second ramp, and a pitch adjustment mechanism,
wherein a first slope of the first ramp faces a second slope of the opposing, second ramp, and wherein a first upper surface of the first slope of the first ramp slopes downwards towards the second ramp to connect to an upper surface of the planar member and a second upper surface of the second slope of the second ramp slopes downwards towards the first ramp to connect to the upper surface of the planar member,
wherein a portion of the upper surface of the planar member separates, and extends between, the first upper surface of the first ramp and the second upper surface of the second ramp,
wherein an outer convex surface of the shell frame or the carriage rides upon, and moves relative to, the first ramp and the second ramp to adjust a pitch of the shell frame relative to the support base,
wherein the pitch adjustment mechanism extends through a pitch adjustment slot in the support base and through the shell frame or through the carriage, and is configured to enable the shell frame or the carriage to slidably move against the first ramp and the second ramp of the support base to adjust the pitch of the shell frame relative to the support base, and
wherein the pitch adjustment mechanism further comprises a pitch adjustment wheel having adjustment teeth that extend through a hole in the support base to engage with adjustment notches in a lower surface of the shell frame and wherein rotation of the pitch adjustment wheel causes the adjustment teeth to engage with the adjustment notches and to move the shell frame relative to the support base causing a change in pitch of the shell frame.

9. The structure of claim 8, wherein the first upper surface of the first ramp includes a first concave surface which includes at least one first movement slot that enables the shell frame or the carriage to slidably move against the first concave surface.

10. The structure of claim 9, wherein the second upper surface of the second ramp includes a second concave surface which includes at least one second movement slot that enables the shell frame or the carriage to slidably move against the second concave surface.

11. A structure for positioning a body part, comprising:
a support base comprising a first concave ramp and an opposing, second concave ramp, wherein a first slope of the first concave ramp faces a second slope of the opposing, second concave ramp and wherein the first slope slopes downwards towards the second concave ramp and the second slope slopes downwards towards the first concave ramp; and
a shell frame, having an inner surface configured to a shape of the body part and an outer convex surface, wherein the outer convex surface of the shell frame is further configured to: ride upon, and move relative to, an upper surface of a carriage, that further resides upon the upper surfaces of the first concave ramp and the second concave ramp, to enable a roll of the shell frame to be adjusted relative to the support base, wherein the structure further comprises:
a roll adjustment mechanism configured to facilitate adjustment of the roll of the shell frame relative to the support base,
wherein the roll adjustment mechanism comprises an adjustment fastener that extends through the carriage and the shell frame, a locking spacer and an adjustment knob and wherein the adjustment knob connects to the adjustment fastener, and
wherein the adjustment knob is rotatable to cause the locking spacer to tighten against a surface of the carriage to lock the shell frame into a specific roll position.

12. A structure, comprising:
a support base configured to be positioned on a flat surface and to receive a shell frame, or a carriage upon which the shell frame rests, and comprising:
a first concave ramp and an opposing, second concave ramp, wherein a slope of each of the first and second concave ramps slopes downwards towards one another and wherein an outer convex surface of the shell frame or the carriage rides upon, and moves relative to, the first concave ramp and the second concave ramp to adjust a pitch of the shell frame relative to the support base; and
a pitch adjustment mechanism, that extends through a pitch adjustment slot in the support base and through the shell frame or through the carriage, and is configured to enable the shell frame or the carriage to slidably move against the first concave ramp and the second concave ramp of the support base to adjust the pitch of the shell frame relative to the support base,
wherein the pitch adjustment mechanism further comprises a pitch adjustment wheel having adjustment teeth that extend through a hole in the support base to engage with adjustment notches in a lower surface of the shell frame and wherein rotation of the pitch adjustment wheel causes the adjustment teeth to engage with the adjustment notches and to move the shell frame relative to the support base causing a change in pitch of the shell frame.

* * * * *

UNITED STATES PATENT AND TRADEMARK OFFICE
CERTIFICATE OF CORRECTION

PATENT NO. : 11,679,053 B2
APPLICATION NO. : 15/859993
DATED : June 20, 2023
INVENTOR(S) : Gregory Nephi Nordgren et al.

Page 1 of 1

It is certified that error appears in the above-identified patent and that said Letters Patent is hereby corrected as shown below:

In the Claims

Column 15, Claim 2, Line 56 should read:
2. The structure of claim 1, wherein the structure Signed and Sealed this
Twenty-second Day of August, 2023

Katherine Kelly Vidal
*Director of the United States Patent and Trademark Office*